(12) United States Patent
Farnan et al.

(10) Patent No.: US 8,821,527 B2
(45) Date of Patent: Sep. 2, 2014

(54) CANNULA TIPS, TISSUE ATTACHMENT RINGS, AND METHODS OF DELIVERING AND USING THE SAME

(75) Inventors: Robert C. Farnan, River Vale, NJ (US); Arielle Drummond, Saddle Brook, NJ (US); Jerry Brightbill, Newton, MA (US); Timothy Walter Robinson, Sandown, NH (US); Richard Wisdom, Mattapan, MA (US); Jonathan O'Keefe, North Attleboro, MA (US); Richard Abraham, Reading, MA (US); Sarah Kostanski, Chelmsford, MA (US); Bryan Fritz, Madison, NJ (US)

(73) Assignee: Circulite, Inc., Teaneck, NJ (US)

( * ) Notice: Subject to any disclaimer, the term of this patent is extended or adjusted under 35 U.S.C. 154(b) by 0 days.

(21) Appl. No.: 13/602,747

(22) Filed: Sep. 4, 2012

(65) Prior Publication Data

US 2013/0060267 A1   Mar. 7, 2013

Related U.S. Application Data

(60) Provisional application No. 61/531,957, filed on Sep. 7, 2011.

(51) Int. Cl.
*A61B 17/00* (2006.01)
*A61M 5/32* (2006.01)

(52) U.S. Cl.
USPC .......................................... 606/190; 604/174

(58) Field of Classification Search
USPC ............. 606/108, 153, 190, 198; 604/164.04, 604/174, 177, 178, 175
See application file for complete search history.

(56) References Cited

U.S. PATENT DOCUMENTS

| | | | |
|---|---|---|---|
| 3,253,594 A * | 5/1966 | Matthews et al. | 604/178 |
| 4,534,761 A * | 8/1985 | Raible | 604/175 |
| 5,279,575 A * | 1/1994 | Sugarbaker | 604/174 |
| 5,391,156 A * | 2/1995 | Hildwein et al. | 606/108 |
| 5,902,316 A * | 5/1999 | Mollenauer | 606/190 |
| 7,798,998 B2 | 9/2010 | Thompson et al. | |
| 2009/0112050 A1 | 4/2009 | Farnan et al. | |
| 2010/0249490 A1 | 9/2010 | Farnan | |
| 2010/0249491 A1 | 9/2010 | Farnan et al. | |

OTHER PUBLICATIONS

U.S. Patent and Trademark Office, International Search Report and Written Opinion in PCT Application Serial No. PCT/US2012/053891, Nov. 13, 2012.
U.S. Patent and Trademark Office, Written Opinion of the International Preliminary Examining Authority in PCT Application Serial No. PCT/US2012/053891, Sep. 12, 2013.
U.S. Patent and Trademark Office, International Preliminary Report on Patentability in PCT Application Serial No. PCT/US2012/053891, Dec. 6, 2013.

* cited by examiner

*Primary Examiner* — Julian W Woo
(74) *Attorney, Agent, or Firm* — Wood, Herron & Evans, L.L.P.

(57) ABSTRACT

A surgical cannula system. The surgical cannula system includes a cannula having a proximal end, a distal end, and a lumen extending therebetween. A tissue attachment ring, being configured to be coupled to a biological tissue, includes a lumen extending therethrough. A locking mechanism has a first locking state, in which the cannula is configured to move with respect to the tissue attachment ring, and a second locking state, in which movement of the cannula with respect to the tissue attachment ring is resisted.

22 Claims, 33 Drawing Sheets

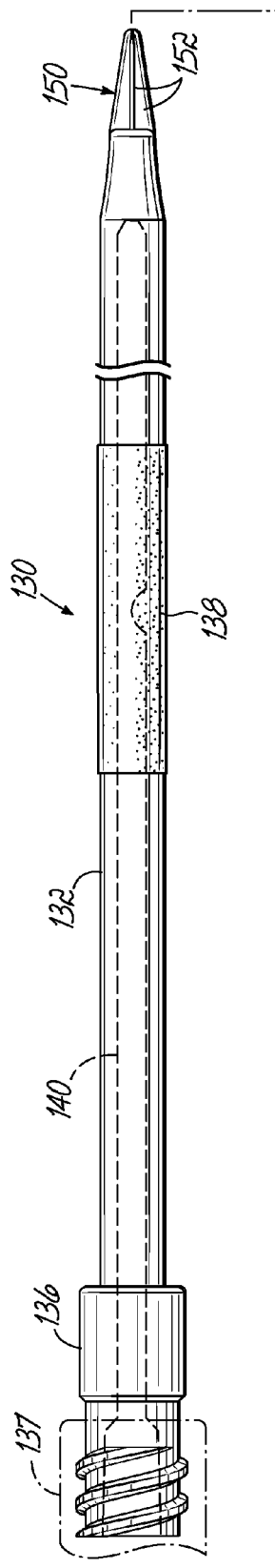
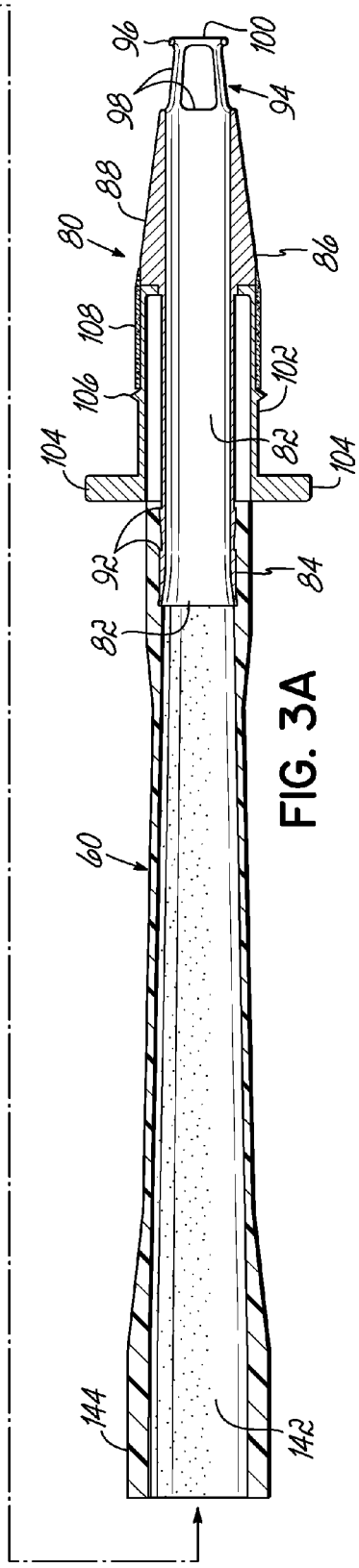
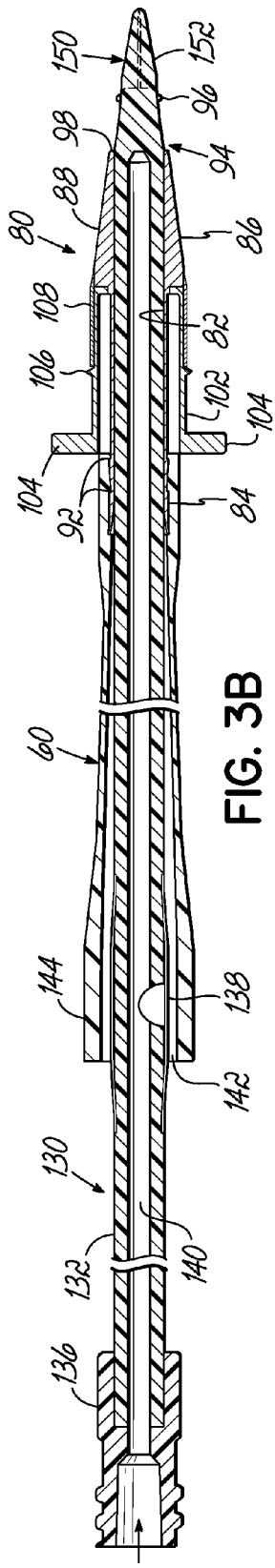
FIG. 3A
FIG. 3B

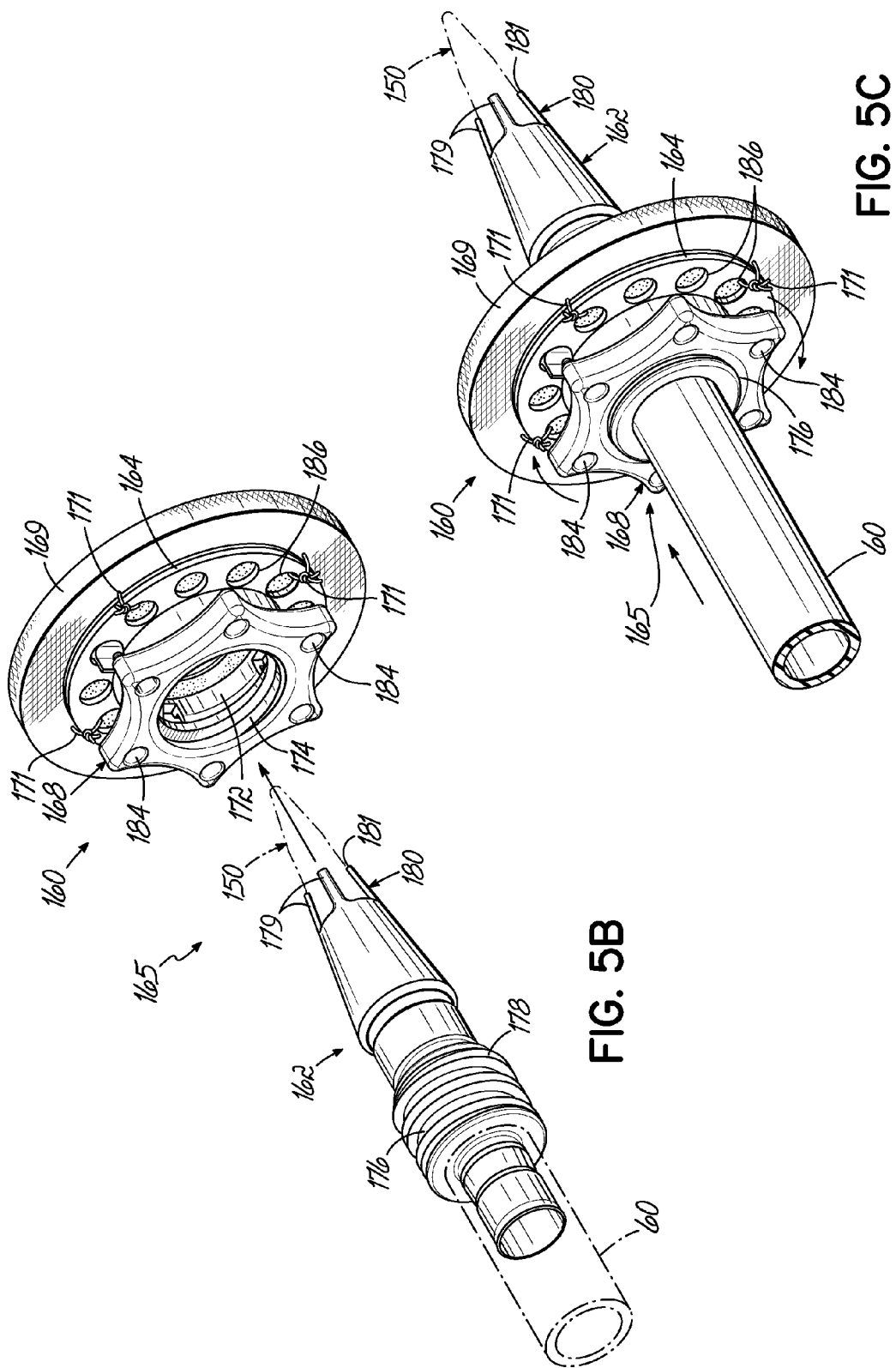

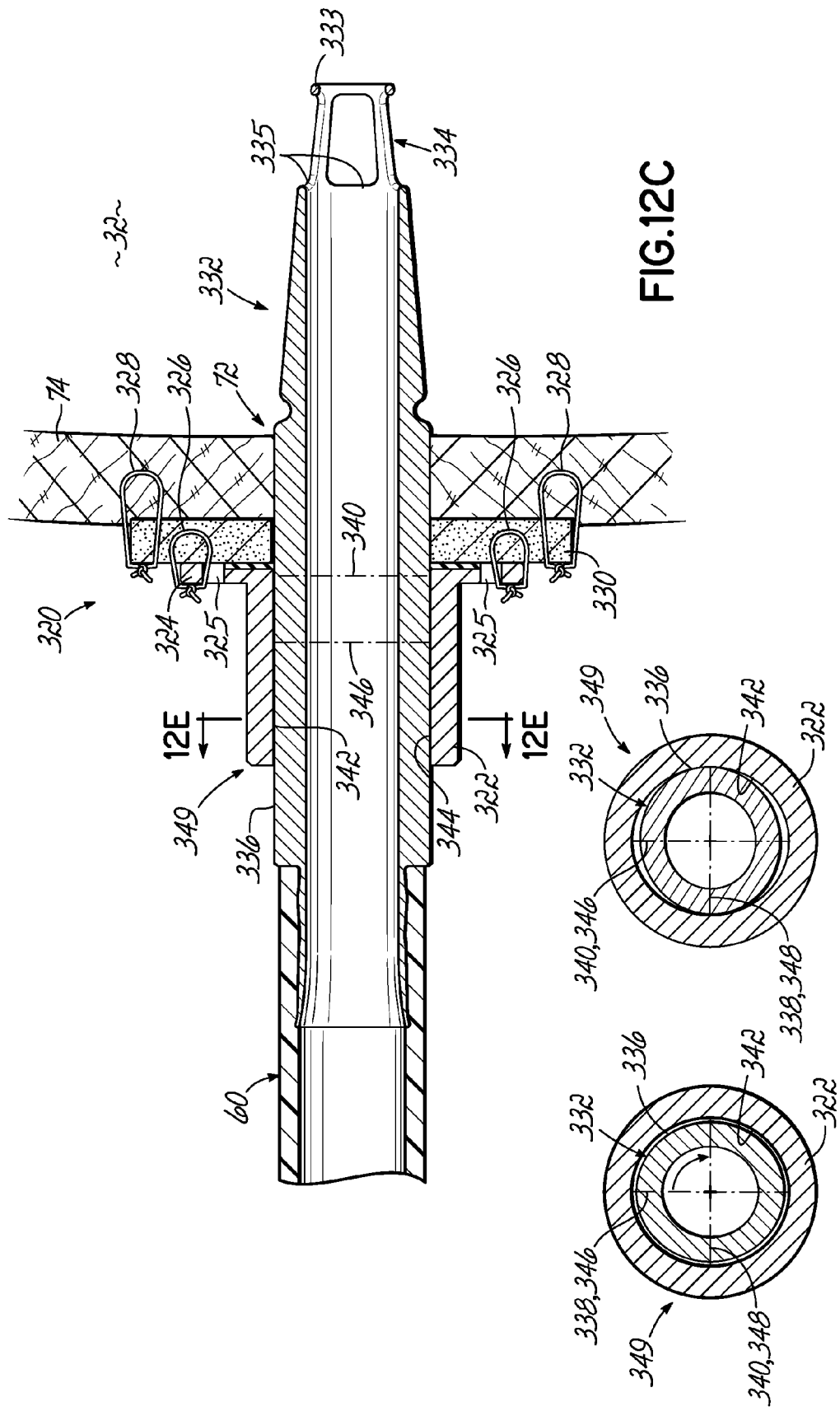

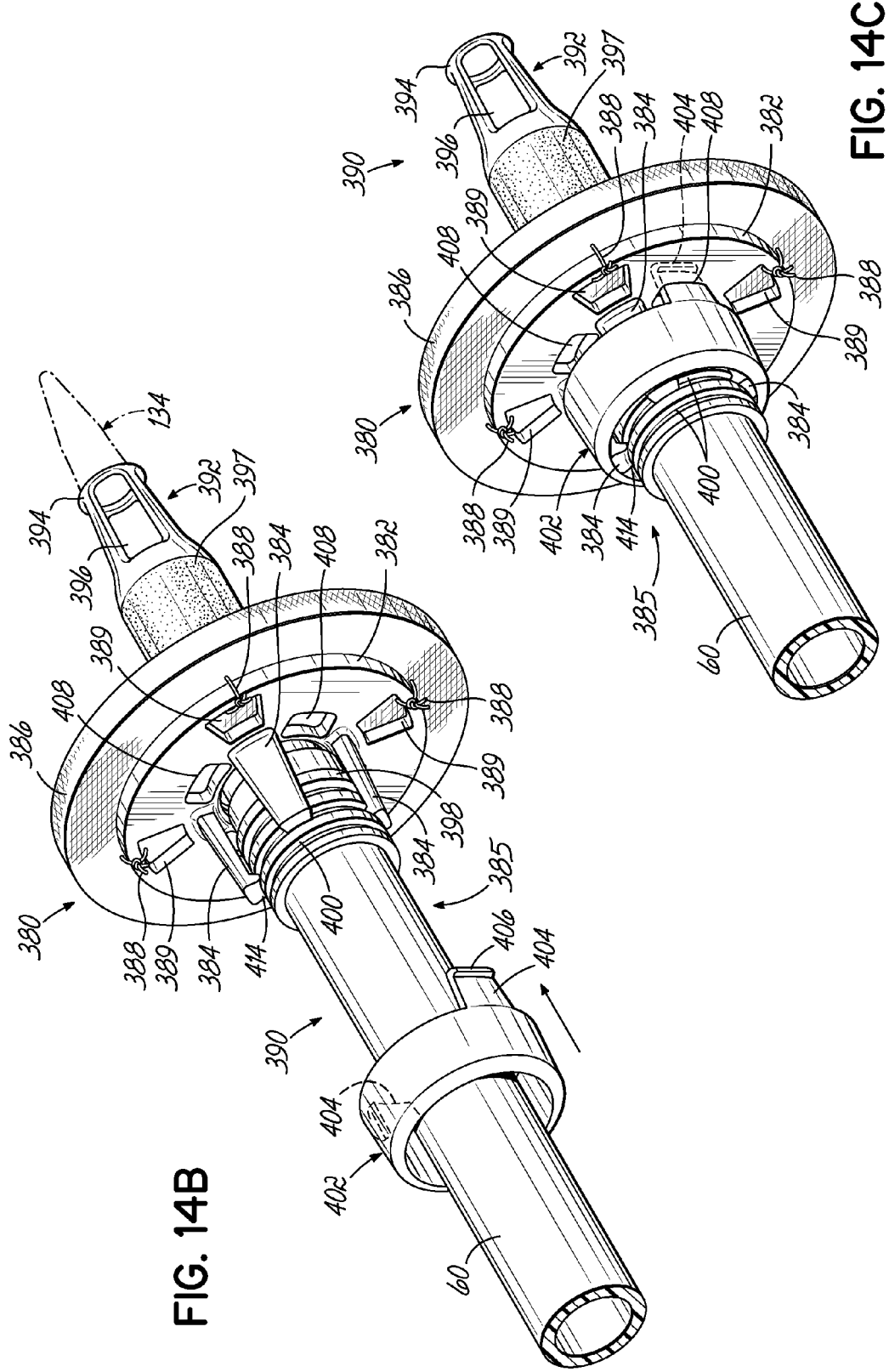

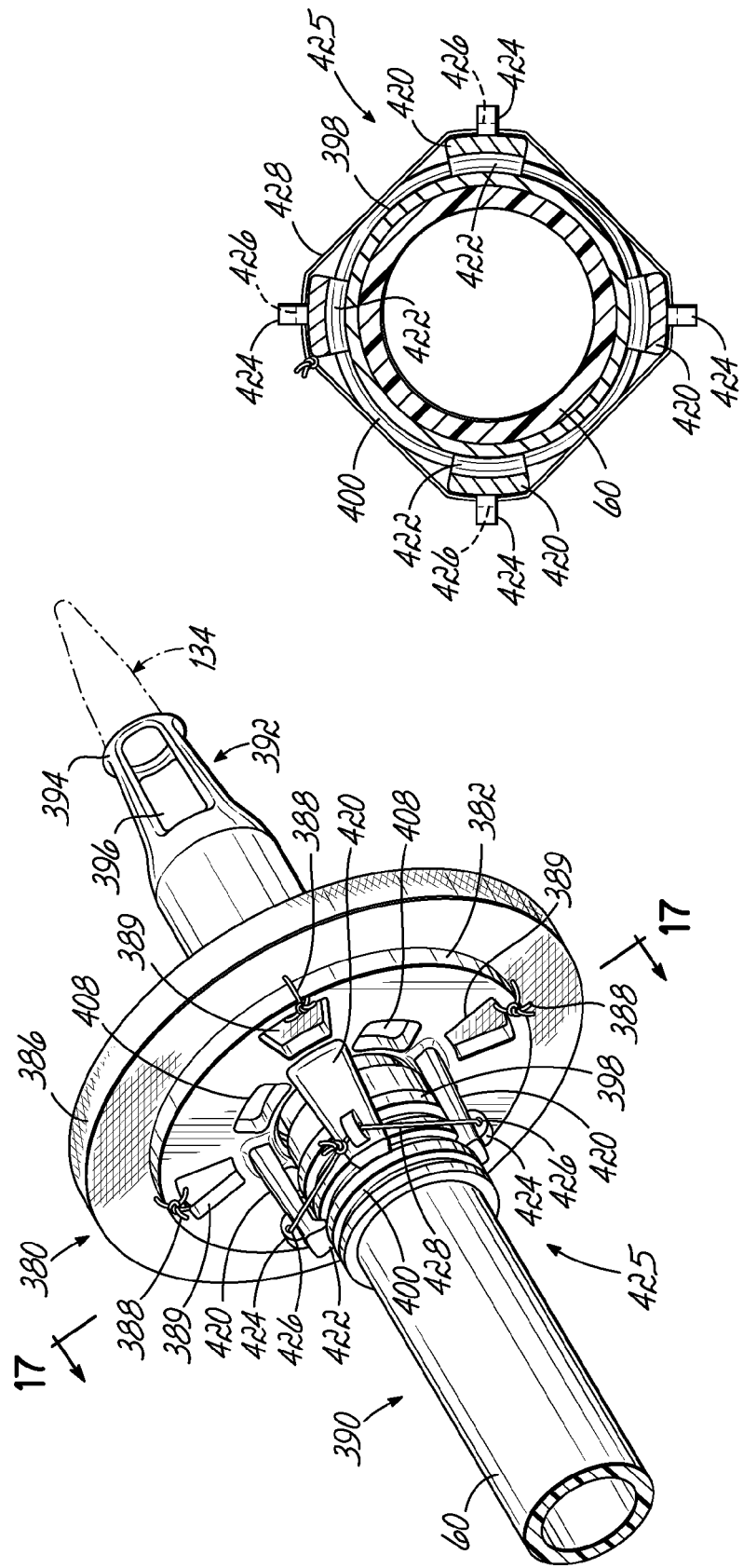

CANNULA TIPS, TISSUE ATTACHMENT RINGS, AND METHODS OF DELIVERING AND USING THE SAME

CROSS-REFERENCE TO RELATED APPLICATION

This application claims the benefit of U.S. Provisional Patent Application Ser. No. 61/531,957, filed on Sep. 7, 2011, the disclosure of which is incorporated by reference herein, in its entirety.

FIELD OF THE INVENTION

The present invention relates generally to medical devices and methods for assisting the conduction of bodily fluids and, more particularly, to devices and methods for securing a cannula to an organ for moving fluid therefrom.

BACKGROUND OF THE INVENTION

Various devices and methods have been utilized to assist in conducting bodily fluids. For instance, blood pumps with inflow and outflow cannulae assist the heart in circulating blood in a patient experiencing congestive heart failure and a transplant organ has either not been located or the patient is not a suitable candidate for the transplant. Accordingly, the blood pump may be fluidically attached to a pumping chamber of the heart and then located remotely. In some configurations, the blood pump may be positioned subcutaneously or submuscularly in a manner similar to a pacemaker, in what is referred to as a "pump pocket." A cannula may then extend, percutaneously or surgically, between the heart and the blood pump. In still another configuration, the pump is configured to pump another bodily fluid and the cannula extends between the pump and a fluid-filled cavity within the body, such as the bladder or kidney for dialysis, urinary obstruction, or infection.

However, known conventional cannula designs are often secured to the tissue surrounding the particular cavity by one or more sutures, which limits the adjustability of the cannula position after it has been secured. Furthermore, when a sewing ring is used in securing the cannula to the tissue, proper placement of the sewing ring relative to the cannula may be time consuming. Therefore, there remains a need for a cannula design that is capable of timely connecting the cannula to a tissue, provides for some adjustability to accommodate the individualistic anatomical differences of each patient, and provides adjustability after securement.

SUMMARY OF THE INVENTION

According to one embodiment of the present invention, a surgical cannula system is described. The surgical cannula system includes a cannula having a proximal end, a distal end, and a lumen extending therebetween. A tissue attachment ring, configured to be coupled to a biological tissue, includes a lumen extending therethrough. The surgical cannula system includes a locking mechanism having a first locking state, in which the cannula is configured to move with respect to the tissue attachment ring, and a second locking state, in which movement of the cannula with respect to the tissue attachment ring is resisted.

The locking mechanism may further include a first locking element that is operably coupled to the tissue attachment ring. A second locking element may be additionally and operably coupled to an outer surface of the cannula.

The locking mechanism may transition between the first and second locking states when the cannula is directed through the lumen of the tissue attachment ring or, alternatively, after the cannula is located within the tissue attachment ring.

The cannula may be secured in at least a first position with respect to the tissue attachment ring and while the locking mechanism is in the second locking state. Other embodiments, the cannula may be secured in a second position, where the first and second positions are discrete positions of the cannula relative to the tissue attachment ring. Still, in other embodiments, the first and second positions may define boundary positions, between which the position of the cannula with respect to the tissue attachment ring is variable and/or non-discrete.

In accordance with another embodiment of the present invention, a surgical cannula system includes a cannula, a tissue attachment ring, and a locking mechanism. The cannula includes a proximal end, a distal end, and a lumen extending therebetween. The tissue attachment ring is configured to be coupled to a biological tissue and has a lumen extending therethrough. The locking mechanism is operably coupled to the tissue attachment ring and is configured to secure a first position of the cannula with respect to the lumen of the tissue attachment ring.

Other embodiments may include a second position of the cannula with respect to the tissue attachment ring. The first and second positions may be discrete positions of the cannula relative to the tissue attachment ring. Still, in other embodiments, the first and second positions may define boundary positions, between which the position of the cannula with respect to the tissue attachment ring is variable and/or non-discrete.

Yet another embodiment of the present invention is directed to a cannula delivery system. A cannula has a lumen through which a shaft extends. An obturator tip on the distal end of the shaft is configured to dilate a puncture in a biological tissue. The shaft also includes an expandable portion that, when expanded, engages an inner surface of the cannula. When the expandable portion is expanded to engage the proximal end of the cannula, the obturator tip is configured to extend away from the distal end of the cannula for dilating the puncture.

Accordingly to still another embodiment of the present invention a method of securing a cannula to a surgical site includes attaching a tissue attachment ring to the surgical site. The tissue attachment ring includes a lumen configured to receive the cannula. The cannula is directed through the lumen of the tissue attachment ring and the biological tissue at the surgical site. A locking mechanism is transitioned from a first locking state, in which the cannula is moveable relative to the tissue attachment ring, to a second locking state, in which a position of the cannula is secured with respect to the tissue attachment ring.

In various aspects of the locking mechanism, the first locking state is transitioned to the second locking state by one or more of forming a frictional fit, threading engagement, ratcheting engagement, utilizing a first locking element, with or without a second locking element and/or an optional third locking element.

BRIEF DESCRIPTION OF THE FIGURES

FIG. 3A is a disassembled, side-elevational view, in partial cross-section, of one exemplary embodiment of a delivery system and the cannula as shown in FIG. 2A, the delivery system having a cutting tip configured to deliver the cannula and tip of FIG. 1 through the tissue of the heart of the patient.

FIGS. 3B and 3C are assembled, cross-sectional views of the delivery system and cannula shown in FIG. 3A.

FIG. 5B is a disassembled, perspective view of the cannula tip and the tissue attachment ring of FIG. 5A.

FIG. 5C is an assembled, perspective view of the cannula tip and the tissue attachment ring of FIG. 5A.

FIGS. 12A-12C are cross-sectional views illustrating the sequence of a method of inserting and securing a cannula tip with a tissue attachment ring with a locking mechanism in accordance with another embodiment of the present invention.

FIGS. 12D and 12E are cross-sectional views taking along the line 12D-12D of FIG. 12B and line 12E-12E of FIG. 12C, respectively.

FIG. 14B is an assembled, perspective view of the cannula tip extending through the tissue attachment ring of FIG. 14A.

FIG. 14C is an assembled, perspective view with the cannula tip secured to the tissue attachment ring by a locking mechanism in accordance with another embodiment of the present invention.

FIG. 16 is an assembled, perspective view of a cannula tip and a tissue attachment ring secured by a locking mechanism in accordance with another embodiment of the present invention.

FIG. 17 is a cross-sectional view of the cannula tip taken along the line 17-17 in FIG. 16.

DETAILED DESCRIPTION

While the various embodiments of the present invention may be useful for use with any organ or cavity within the body, including, for example, the kidneys, the bladder, the stomach, or the heart, the illustrated examples included herein are drawn specifically to applications with the heart.

Figure 1:
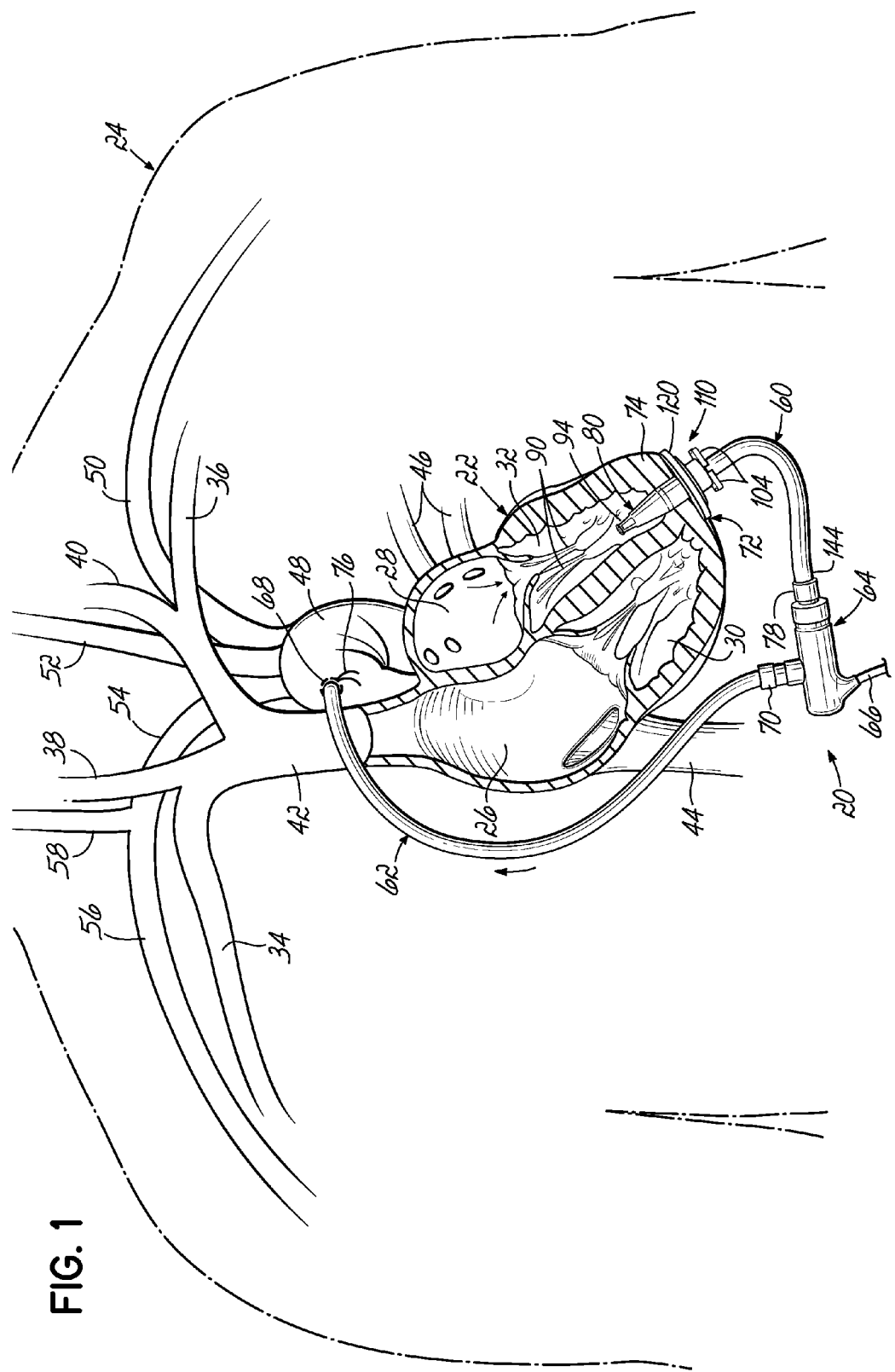
FIG. 1 is a schematic representation of chest anatomy and illustrates a cardiac assist system having a cannula coupled to the heart of the patient with a tip in accordance with one embodiment of the present invention.

FIG. 1 illustrates one embodiment of an implanted circulatory assist device 20 implanted in a pediatric patient. For illustrative purposes, certain anatomy is shown including the heart 22 of the patient 24 having a right atrium 26, a left atrium 28, a right ventricle 30, and a left ventricle 32. Blood from the right and left subclavian veins 34, 36 and the right and left jugular veins 38, 40 enters the right atrium 26 through the superior vena cava 42 while blood from the lower parts of the body enters the right atrium 26 through the inferior vena cava 44. The blood is pumped from the right atrium 26, to the right ventricle 30, and to the lungs (not shown) to be oxygenated. Blood returning from the lungs enters the left atrium 28 via pulmonary veins 46 and is pumped into the left ventricle 32. Blood leaving the left ventricle 32 enters the aorta 48 and flows into the left subclavian artery 50, the left common carotid 52, and the brachiocephalic trunk 54, including the right subclavian artery 56 and the right common carotid 58.

With respect to the implanted circulatory assist device 20, two cannulae 60, 62 (inflow and outflow, respectively) extend between cardiovascular structures and a pump 64, which may be any implantable or extracorporeal pump that is radially-and/or axially-driven. Those skilled in this art, however, recognize that other types of pumps may be used in other embodiments but may include pumps such as those described in U.S. patent application Ser. No. 11/627,444, published as 2007/0197854, which is incorporated herein by reference in its entirety, or commercially-available pumps, such as the SYNERGY Pocket Micro-Pump from CircuLite, Inc. (Saddle Brook, N.J.).

A cable 66 may extend transdermally from the pump 64 to a position in the abdomen where the cable 66 exits the patient 24 and connects to a power supply (not shown). Suitable power supplies may be any universal-type power supply that sends power to the pump 64 via the cable 66 and may include, but is not limited to, a rechargeable battery pack.

As illustrated, the physician may position the pump 64 at least subcutaneously and, optionally, submuscularly in a pump pocket (not shown).

The outflow cannula 62 extends from an outflow port 70 of the pump 64 to an arterial access site 68, which is specifically illustrated herein as being within the aorta 48. The outflow cannula 62 may be any suitable intravascular cannula device constructed from materials, such as an extruded aliphatic, polycarbonate-base polyurethane; aliphatic polyether polyurethane; aromatic polyether polyurethane; aromatic polycarbonate based polyurethane; silicone modified polyurethane; or silicone. Antimicrobial agents may be embedded within the outflow cannula material prior to the forming process to effectively reduce or eliminate the presence of bio-film and reduce the potential for infection. Alternatively, the antimicrobial agent may be applied to the surface of the outflow cannula 62 after the molding process is complete.

A reinforcing structure (not shown) may be included in the outflow cannula construction to reduce the likelihood of kink formation. The reinforcing structure may be, for example, a braided or coiled construction of a metal wire, such as stainless steel or titanium wire, or a polymeric material, such as KEVLAR (E.I. du Pont de Nemours and Co., Wilmington, Del.). The construction material may have various cross-sectional shapes, including, but not limited to, round and rectangular. If a round wire is used, the wire diameter may vary from about 0.001 inch (0.0254 mm) to about 0.005 inch (0.127 mm). If the material has a rectangular cross-section, the rectangle may have a height ranging from about 0.001 inch (0.0254 mm) to about 0.005 inch (0.127 mm) and a width ranging from about 0.003 inch (0.0762 mm) to about 0.010 inch (0.254 mm).

The outflow cannula 62 is configured to be secured to the arterial access site 68 by one or more sutures 76 and/or one or more anastomotic connectors (not shown), such as those taught in U.S. patent application Ser. No. 12/829,425, the disclosure of which is incorporated herein by reference, in its entirety.

Referring still to FIG. 1, the inflow cannula 60 is shown to extend between an inflow port 78 of the pump 64 and the apex 74 of the heart 22. The inflow cannula 60 may be constructed in a manner that is similar to the outflow cannula 62; however, other construction materials may be incorporated as desired.

The inflow cannula 60 includes a distally-positioned tip 80 that extends through the apex 74 and into the volume of the left ventricle 32. The tip 80 may be constructed from a metallic material, such as titanium, a titanium alloy, stainless steel, or platinum. The tip 80, when constructed from a metallic material, may include a sintered section or at least a portion covered by a fabric that promotes the in-growth of tissue. Alternatively, the tip 80 may be molded from a thermoset material, such as silicone, or a thermoplastic material, such as polyurethane. An example of a polyurethane that may be used is CARBOTHANE (Lubrizol Advanced Materials, Inc., Cleveland, Ohio). If a relatively conformable design is desired, the tip 80 may be constructed from a thermoset or thermoplastic material having a durometer ranging from about shore 25A to about shore 90A. If a relatively rigid design is desired, the tip 80 may be constructed from a thermoset or thermoplastic material having a durometer ranging from about shore 55D to about shore 90D.

To minimize the chance of thrombus formation, the molding process may include an insert molding process that eliminates parting lines, i.e., those places where a mismatch of material may occur. Use of the insert molding process results in a luminal surface, which is in direct contact with blood flowing through the tip 80, that is smooth and seamless. Accordingly, it is not necessary to coat an inner surface of the lumen 82 (FIG. 2A) with an anti-thrombotic material, yet the coatings may be included if so desired.

To increase hemocompatibility, the tip 80 may be polished to minimize irregularities resulting from the machining process. The highly polished surface minimizes proliferation of tissue growth, hence minimizing the likelihood that tissue will grow over the tip 80 and occlude blood flow into the inflow cannula 60.

Figure 2A:
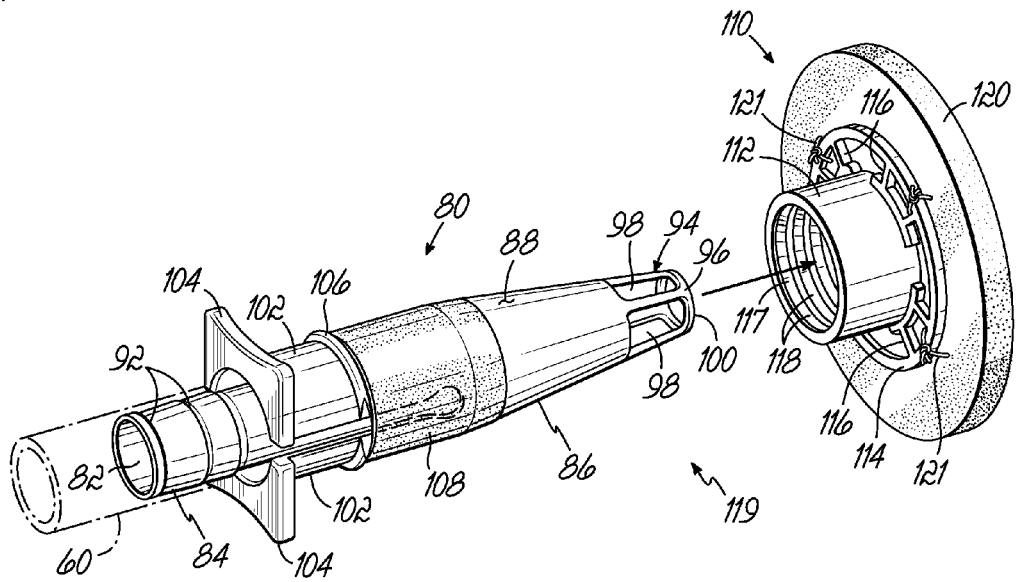
FIGS. 2A and 2B are perspective views of the tip shown in FIG. 1.
Figure 2B:
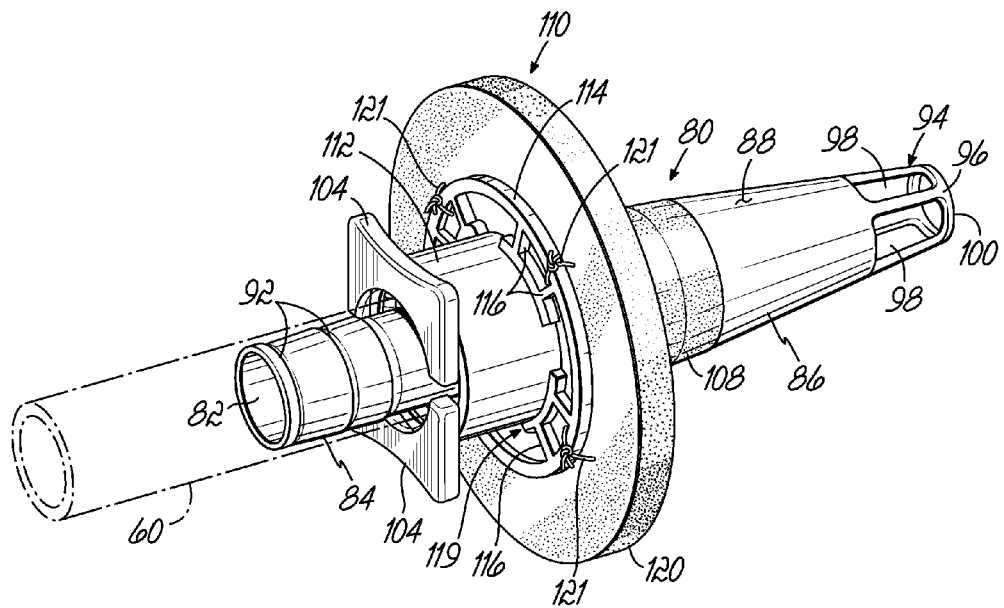

Referring now to FIGS. 2A and 2B, additional details of the tip 80 may be seen. For example, while the diameter of the lumen 82 may be constant throughout the length of both the proximal and distal ends 84, 86 of the tip 80, an outer surface 88 of the tip 80 may be discontinuous. The outer surface 88 may converge, or taper, such as a frusto-conical shape, distally from about a mid-point of the tip 80, and then extend therefrom with a continuous outer diameter. The length of the frusto-conical shape portion of the tip 80 may range, generally, from about 0.5 cm to about 5 cm and, more specifically, from about 0.5 cm to about 2 cm in pediatric patients and about 0.5 cm to about 5 cm in adult patients. These dimensions are suitable to reduce the likelihood of the tip 80 interfering with the mitral valve leaflets 90 (FIG. 1) within the left ventricle 32 (FIG. 1).

One or more barbs 92 may be included on the proximal end 84 to retain the inflow cannula 60 to the tip 80. On the distal end 86, the tip 80 may include a distal cage 94 having a distally-positioned ring 96 and a plurality of openings 98 extending from the ring 96. The plurality of openings 98 and the ring 96 are configured to permit blood to be continuously withdrawn from the left ventricle 32 (FIG. 1) and into the lumen 82 of the tip 80, even when a distal tip end 100 becomes obstructed or occluded, such as by the mitral valve leaflets 90 (FIG. 1) or an adjacent wall of the heart, respectively.

The plurality of openings 98 may include a variety of shapes, shown here as four apertures, in fluid communication with the lumen 82; however, any number of openings 98, or apertures, of various shapes or sizes may be used. Further examples of suitable tip structures are shown in U.S. patent application Ser. No. 12/392,623, published as 2009/0182188, the disclosure of which is incorporated herein in its entirety.

One or more outwardly biased arms 102 may be coupled to the tip 80 between the proximal and distal ends 84, 86. As shown in FIGS. 2A and 2B, the two diametrically-opposed biased arms 102 are coupled to and extending from the tip 80 and terminate with enlarged tabs 104. A locking element 106, shown specifically as a pawl 106 extending concentrically across the biased arms 102, is configured to secure the tip 80 to the apex 74 (FIG. 1), specifically, or an inflow access site 72 (FIG. 1) generally, in a manner that is described in detail below. A sleeve 108 may be positioned over the biased arms 102, without extending over the pawl 106, to secure the biased arms 102 to the tip 80. The sleeve 108 and/or a portion of the outer surface 88 of the tip 80 may include a tissue in-growth material, configured to create a scaffolding for controlled cell growth on the outer surface 88 of the tip 80.

With reference now to FIGS. 1 and 2A, the tip 80 is generally configured to cooperate with a tissue attachment ring 110 that is surgically coupled to the inflow access site 72. As is shown, the tissue attachment ring 100 may be coupled to the inflow access site 72 with one or more sutures 156 (FIG. 4A), and is thus referred to as a sewing ring. However, it would understood that the tissue attachment ring 110 may be coupled to the inflow access site 72 by any securement structure, such as staples, adhesive, or others that are known to those of ordinary skill in the art.

Referring to FIGS. 1, 2A, and 2B, the sewing ring 110 includes a molded body 112 with a distally-positioned, radially-extending band 114 having a plurality of spokes or ribs 116 extending therebetween. A lumen 117 of the molded body 112 includes another locking element 118 of a locking mechanism 119. The first locking element 118, for example, is a dentate surface in the lumen 117 of the molded body 112, the dentate surface 118 being sized and shaped to receive the second locking element 106 of the locking mechanism 119, e.g., the pawl 106 of the tip 80.

A tissue in-growth band 120 may be coupled to a distal end surface of the radially-extending band 114 by one or more sutures 121. The tissue in-growth band 120 may be constructed from a porous polymeric material, such as expanded polytetrafluoroethylene (ePTFE), a woven polyester fabric tubing (e.g., DACRON brand of polyester fiber), velour, or other like materials for creating a scaffolding for cell growth.

Delivery of the inflow cannula 60 with the tip 80 may be facilitated with a delivery system 130 in accordance with one embodiment of the present invention. One suitable delivery system 130 is illustrated with the inflow cannula 60 in FIG. 3A and includes a shaft 132 having a distally-positioned cutting obturator tip 150 and a proximally-positioned hub 136 with a multi-lumen luer hub 137. The multi-lumen luer hub 137 is configured to be coupled to an inflation fluid supply (not shown), and an expandable portion 138, for example, a balloon located on the shaft 132. A lumen 140 within the shaft 132 extends from the hub 136 to the balloon 138 for supplying an inflation fluid.

The shaft 132 may be constructed from any material of suitable column strength to overcome the insertion forces required to pass through a biological tissue. Appropriate materials may include metal tubing, such as stainless steel or nickel titanium tubing, or rigid polymers, such as polyether ether ketone ("PEEK") or nylon.

Figure 3C:
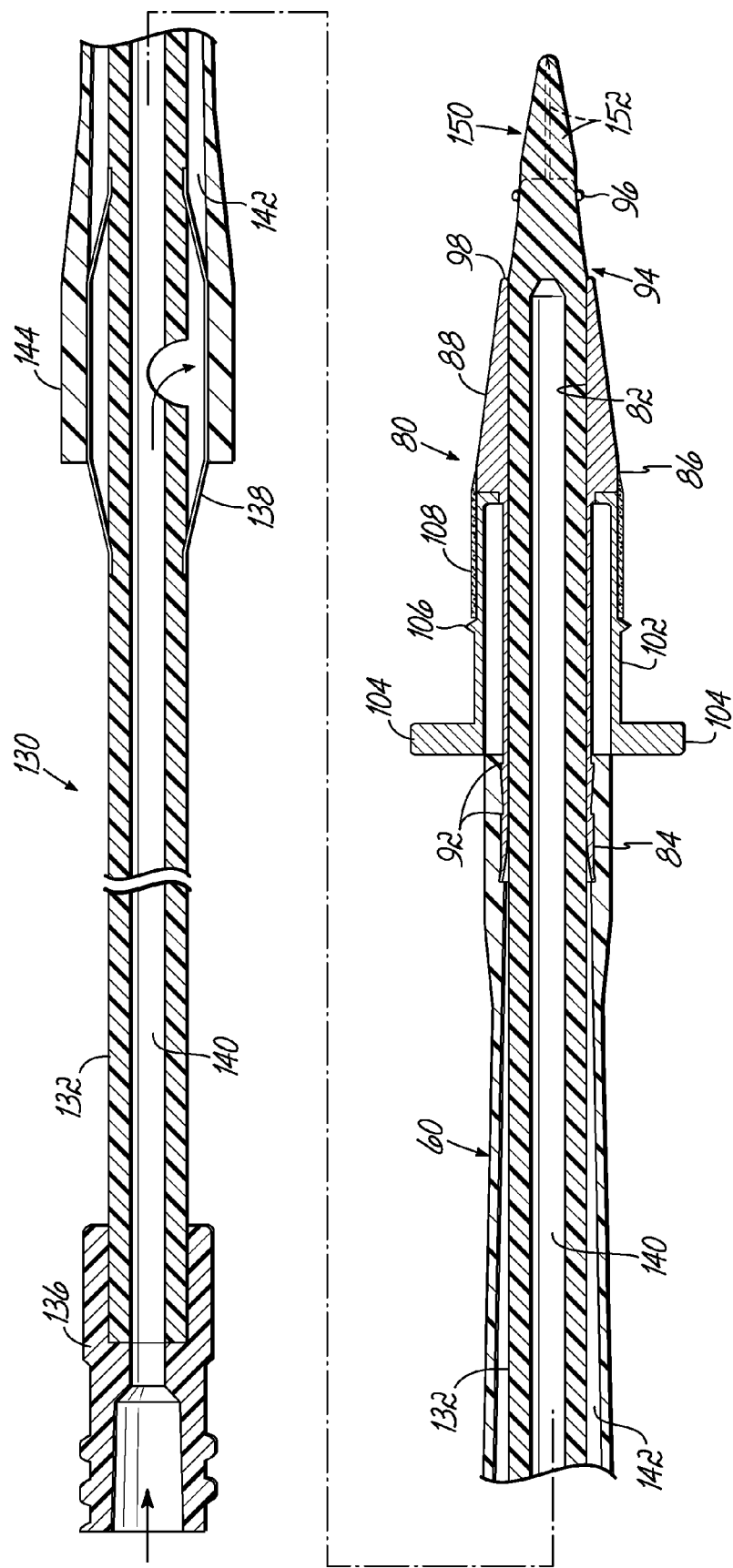
Figure 3D:
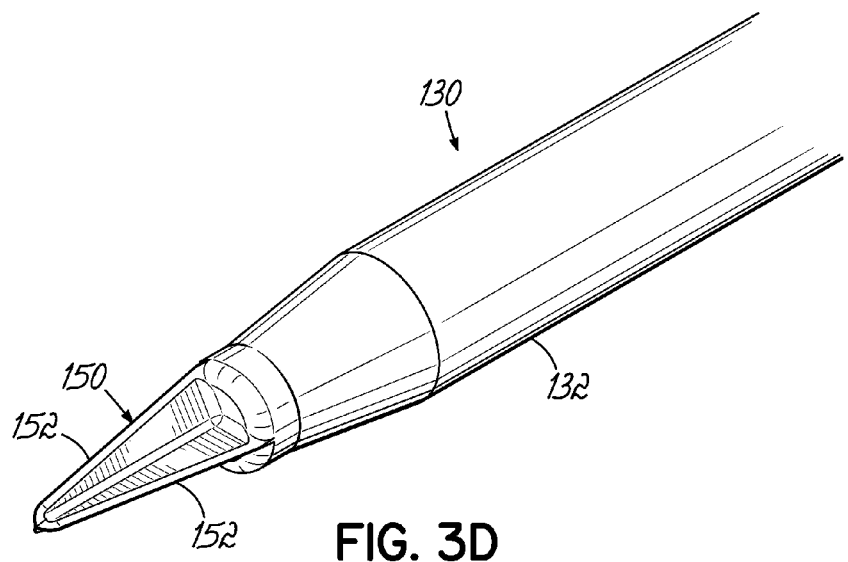
FIG. 3D is a perspective view of the cutting tip of FIG. 3A.
Figure 3E:
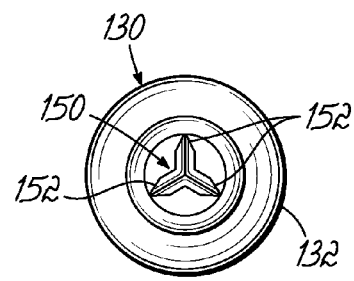
FIG. 3E is a front view of the cutting tip of FIG. 3D.

The cutting obturator tip 150 may include at least one cutting blade 152, though three or more cutting blades 152, as shown in the distal end view of FIG. 3E, may be preferred to reduce the likelihood of tearing tissue. The cutting blades 152 may be constructed from the same material as the shaft 132, particularly stainless steel or nickel titanium, and machined to a razor-sharp edge. Otherwise, the cutting blades 152 may be separately machined and then affixed to the distal end of the shaft 132. The blades 152 enable or facilitate insertion of the delivery system 130 without the need for a preemptive puncture through the tissue.

It will be readily appreciated that the shapes of the distal cage 94 on the tip 80 of the inflow cannula 60 and the cutting obturator tip 150 of the delivery system 130 may be complimentary, i.e., the shapes cooperate in a manner that facilitates insertion of the tip 80 through the biological tissue. In other words, the shape of the distal cage 94 matches the shape of the cutting obturator tip 150 to operate as a vascular dilator and facilitate a smooth insertion of the tip 80. Further, the matching shapes of the cutting obturator tip 150 and the distal cage 94 reduces the chance that tissue is captured or snagged between the cutting obturator tip 150 and the distal cage 94 during tip insertion. As shown in the assembled illustrations of FIGS. 3B and 3C, the shaft 132 of the delivery system 130 extends through the lumen 142 of the inflow cannula 60 and the cutting obturator tip 150 extends, at least partially, beyond the distal cage 94. The balloon 138, when expanded, provides a locking relationship between the inflow cannula 60 and the delivery system 130 at a proximal end of the inflow cannula 60. In that regard and with respect to the particular illustrative embodiment, at inflation, the balloon 138 expands and contacts an inner surface of a proximal hub 144 of the inflow cannula 60. The contact resists movement of the inflow cannula 60 relative to the delivery system 130 and is shown in yet greater detail in FIG. 3C. The inflated balloon 138 also provides the additional benefit of limiting the bleeding back through the inflow cannula 60 during insertion of the tip 80. While not shown, the lumen 142 of the cannula 60 may be replaced with a multi-lumen design that would accommodate a guide-wire or other components in addition to the delivery system 130.

Figure 3F:
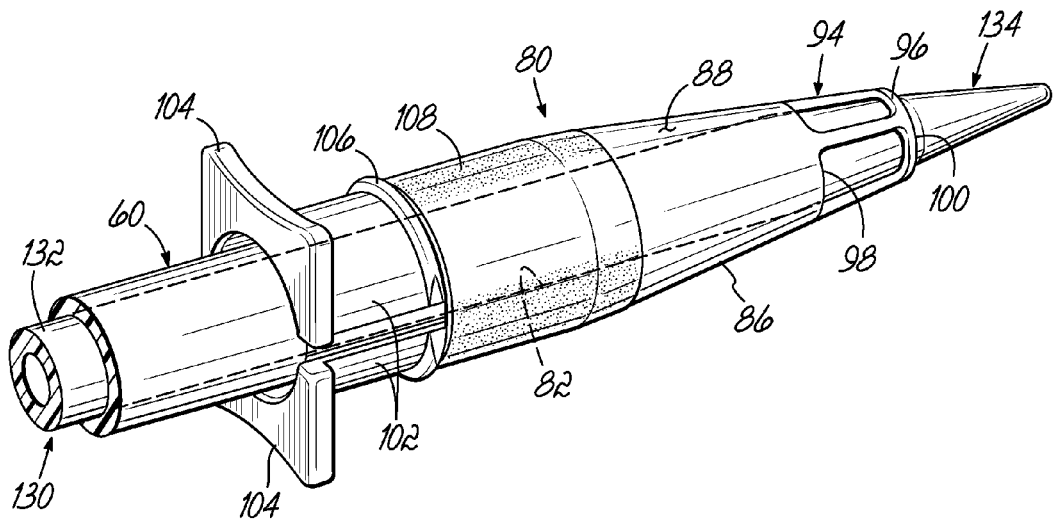
FIG. 3F is an assembled, perspective view of the cannula with a delivery system in accordance with another embodiment of the present invention.

In some embodiments, such as the embodiment shown in FIG. 3F, the distally-positioned cutting obturator tip 150 (FIG. 3A) of the delivery system 130 may be replaced with an obturator tip 134.

With the details of the inflow cannula 60, the tip 80, the delivery system 130, and one embodiment of the locking mechanism 119 provided in some detail, delivery and insertion of the inflow cannula 60 along with the transition of the locking mechanism 119 from a first locking state (FIG. 4B) to a second locking state (FIG. 4C) may be described with reference to FIGS. 1 and 4A-4C. Prior to the procedure shown FIG. 4A, the physician has opened the thoracic cavity by splitting the sternum (not shown) or provided an opening between successive ribs (not shown) to expose the heart 22. The location of the inflow access site 72 on the apex 74 of the heart 22 is determined and the sewing ring 110 attached thereto. The sewing ring 110 may be previously manufactured with the molded body portion 112 coupled to the tissue in-growth band 120, for example, with the one or more sutures 121. As is shown, the sewing ring 110 may be positioned with one or more pledgets 154 between the tissue in-growth band 120 and the apex 74. The physician secures the sewing ring 110 with one or more sutures 156 that extend through the tissue in-growth band 120, via the plurality of ribs 116 of the molded body 112. A puncture wound 158 may then be created centrally through the sewing ring 110. Alternatively, the cutting obturator tip 150 may be directed through the tissue without the puncture wound 158.

Figure 4A:
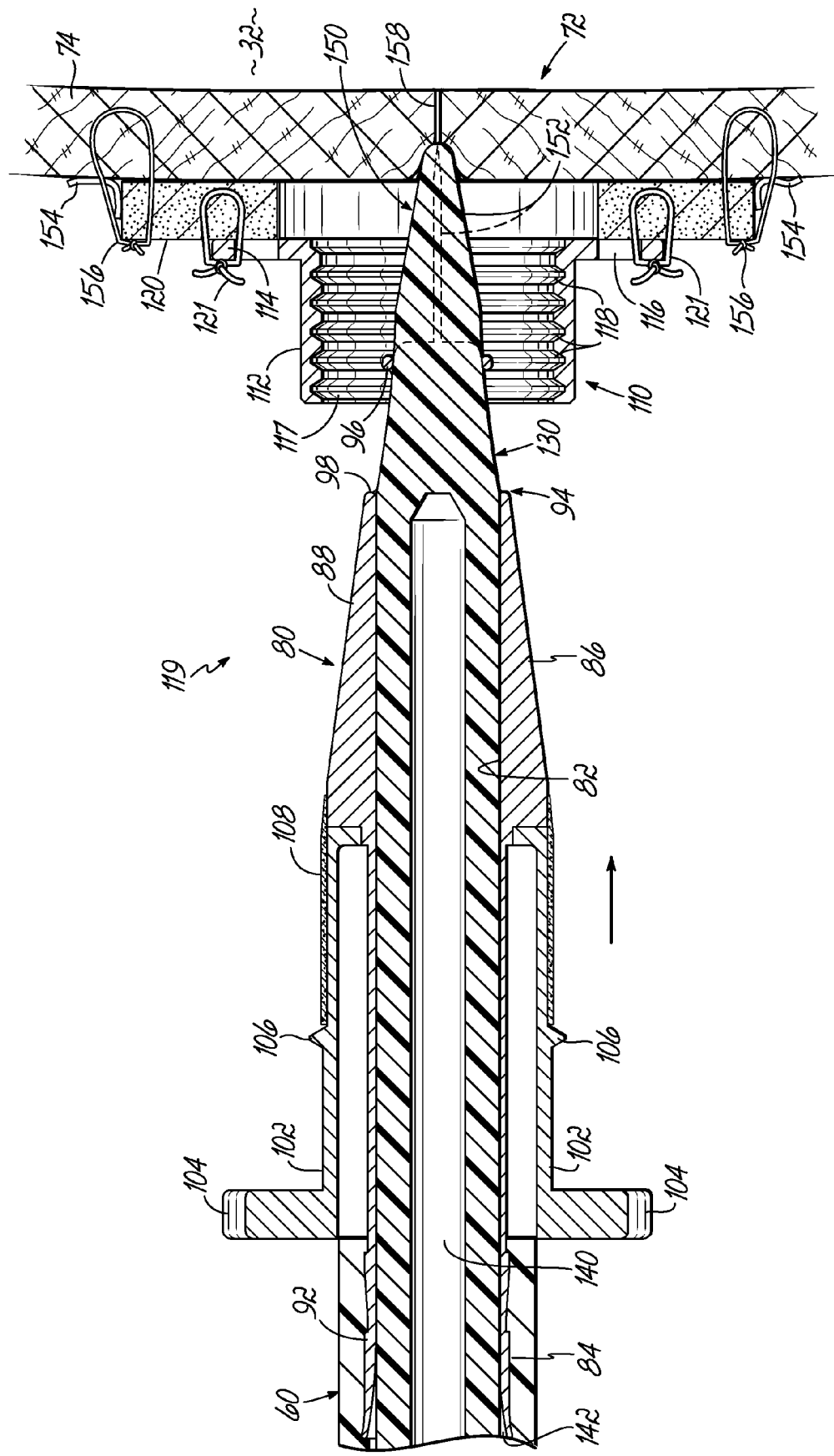
FIGS. 4A-4C are cross-sectional views illustrating the sequence of an exemplary method of inserting and securing the cannula and tip of FIG. 1 with a locking mechanism in accordance with one embodiment of the present invention.

With the sewing ring 110 coupled to the inflow access site 72 and the puncture wound 158, if desired, created and now with reference to FIG. 4A, the physician advances the inflow cannula 60 with the delivery system 130, in locking relation with the inflow cannula 60 by inflation of the balloon 138 (FIG. 3A), through the molded body 112 of the sewing ring 110. With further advancement, the distally-positioned cutting obturator tip 150 dilates the puncture wound 158 and enters the volume of the left ventricle 32.

Figure 4B:
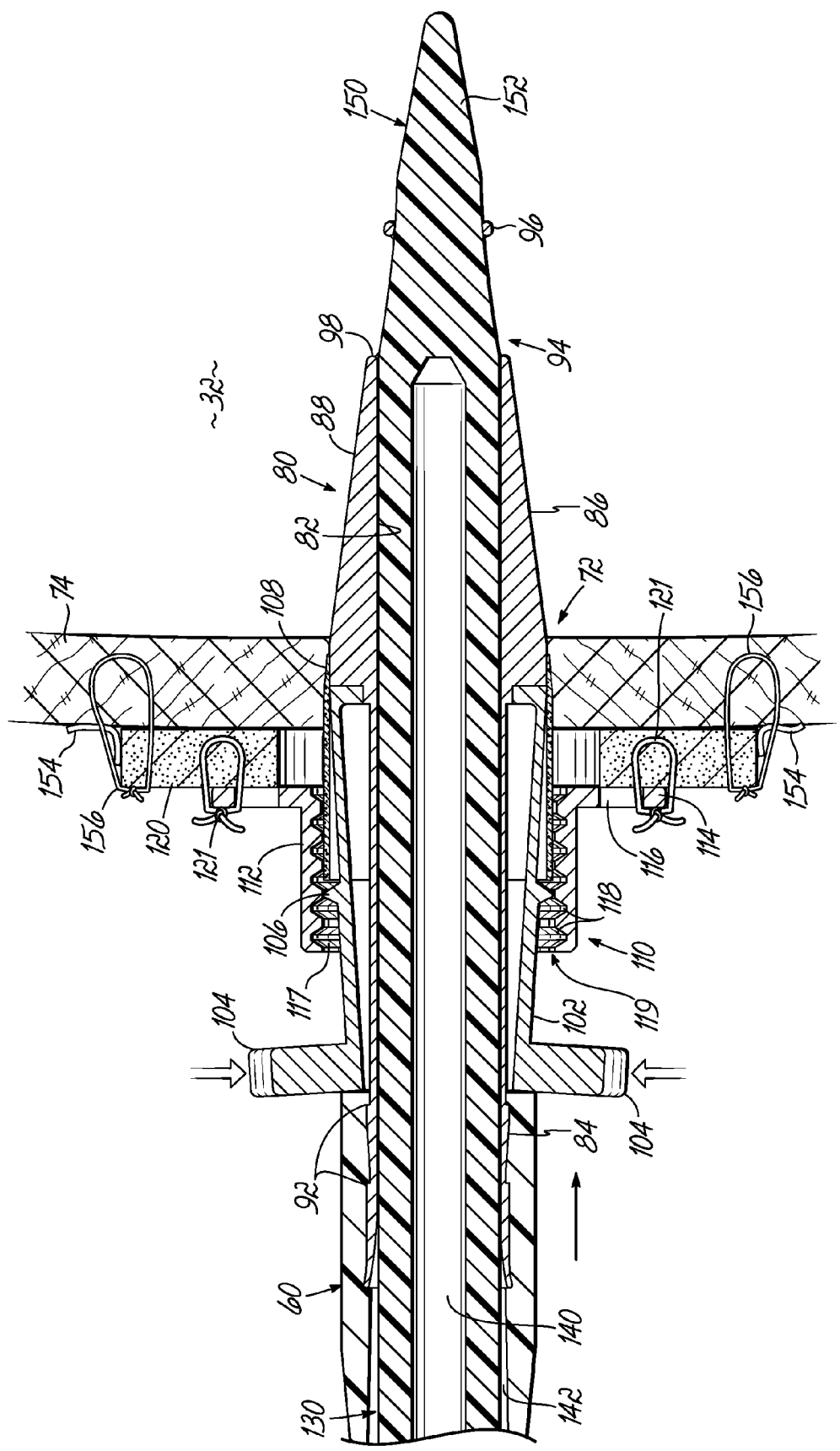

In FIG. 4B, the physician has continued advancing the inflow cannula 60 and the delivery system 130 such that the pawl 106 of the biased arms 102 lies adjacent to a proximal edge of the molded body 112 of the sewing ring 110. By inwardly biasing the enlarged tabs 104, the physician inwardly deflects the arms 102, which also provides a slight inward deflection of the pawl 106 such that the pawl 106 in a first locking state, may be advanced over the dentate surface 118 and into a select one tooth. Further advancement of the tip 80 into the molded body 112 continues so long as the first locking state is maintained by inwardly pressing on enlarged tabs 104. Releasing the tabs 104 releases the pawl 106 to the second locking state, in which the pawl 106 freely deflect outward to its relaxed state and engages the select tooth of the dentate surface 118 and secures the position of the tip 80 relative to the sewing ring 110. Further inward biasing of the pawl 106, i.e., transitioning the pawl 106 back to the first locking state, allows the tip 80 to move with respect to the sewing ring 110 to another position, which may then be secured by again releasing the pawl 106 to the second locking state.

The physician may investigate the position of the tip 80 by a suitable remote visualization technique, such as real time fluoroscopy or echo. For visualization, at least a portion of the tip 80 comprises a radiopaque material, such as platinum-iridium, stainless steel, tungsten, or tantalum. The physician may then adjust the location of the tip 80, forward and reverse, relative to the sewing ring 110, to a select a cannula position with respect to the sewing ring 110, which is directly related to a tip depth residing within the left ventricle 32.

Figure 4C:
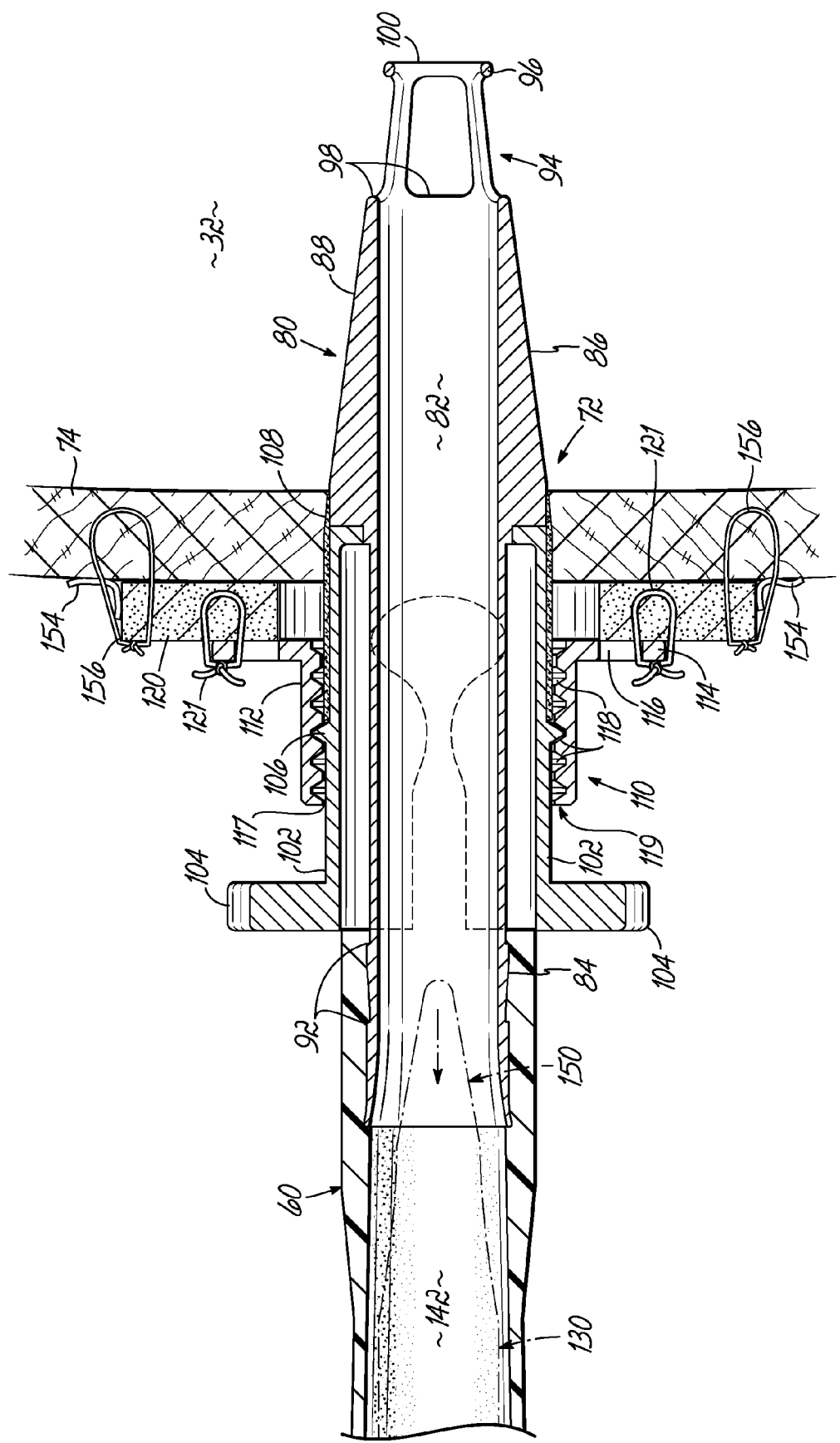

With the tip 80 properly positioned, and with reference to FIGS. 3C and 4C, the physician may then deflate the balloon 138 by removing inflation fluid from the lumen 140 of the shaft 132 through the hub 136. Balloon deflation releases the constraint placed on the inner surface of the inflow cannula hub 144 and allows the physician to retract the delivery system 130 from the inflow cannula 60. After removal, the hub 144 of the inflow cannula 60 may be coupled to the inflow port 78 (FIG. 1) of the pump 64 (FIG. 1).

Figure 5A:
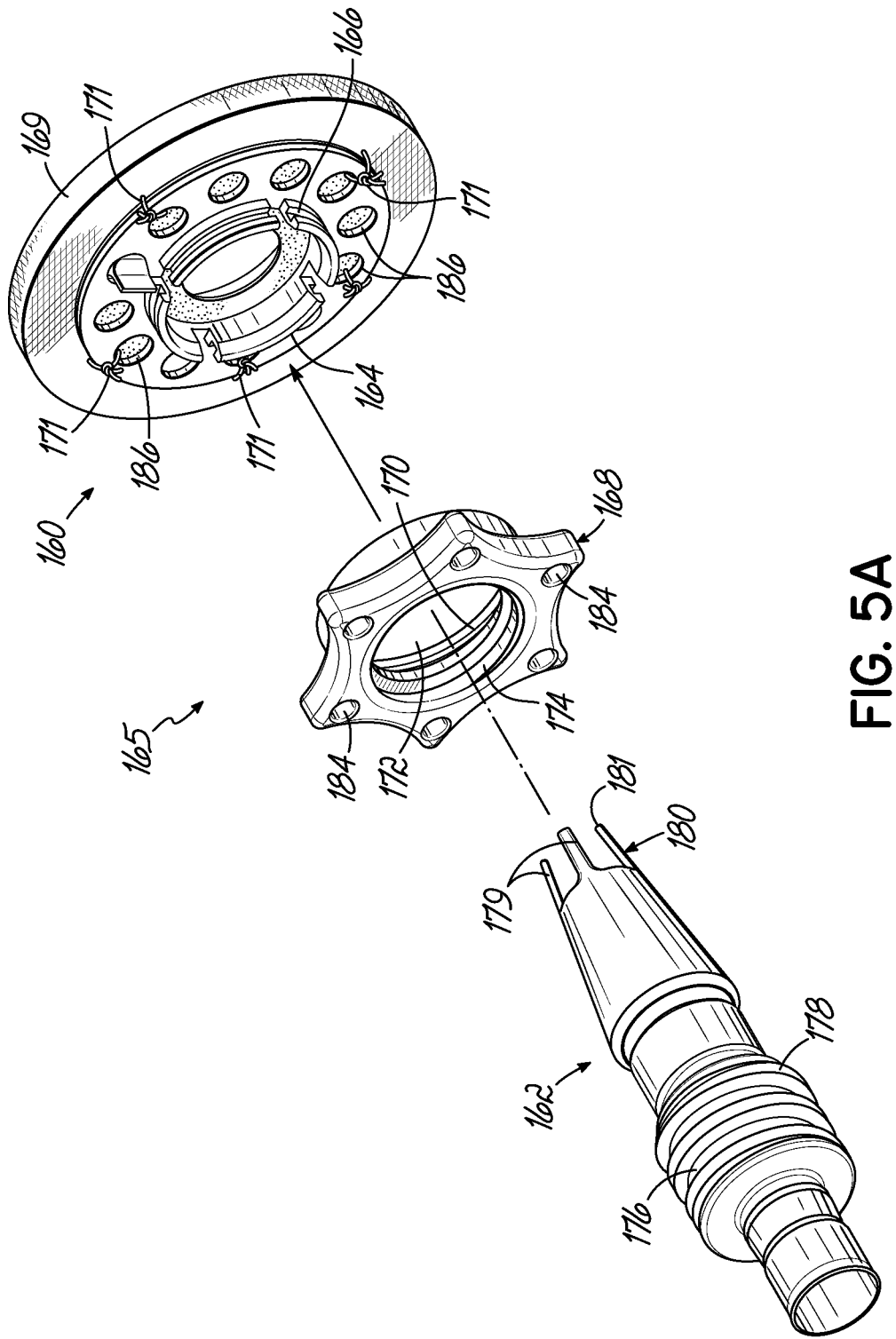
FIG. 5A is an exploded view of a cannula tip and a tissue attachment ring with another locking mechanism in accordance with another embodiment of the present invention.

Turning now to FIGS. 5A-5C, a tissue attachment ring 160 (illustrated and described as a sewing ring) and a cannula tip 162 in accordance with another embodiment of the present invention are described. In FIG. 5A, the sewing ring 160 includes a molded body 164 having an annular groove 166 that is configured to receive a first locking element 168 of a locking mechanism 165, that is shown herein as including a threaded nut. A tissue in-growth band 169 is coupled to the distal end of the molded body 164, for example, via one or more sutures 171. The threaded nut 168, which may be constructed from a sufficiently rigid polymeric material, has a distally-positioned ridge 170 that is received by the annular groove 166 such that the threaded nut 168 freely rotates about the molded body 164 of the sewing ring 160.

The threaded nut 168 and the molded body 164 include a lumen 172 through which the tip 162 is inserted. The lumen 172 at the molded body 164 includes a continuous thread 174 that is sized and shaped to interact with the second locking element 176, specifically illustrated herein as threads on an proximal end 178 of the tip 162. Besides the threads 176, the tip 162, itself, may include a distal cage 180 that is similar to the structure shown in FIG. 2A; however, the distal cage 180 of the instant embodiment of the tip 162 is truncated and does not include a distal ring 96 (FIG. 2A) and thus includes one or more prongs 179 extending to a distal tip end 181.

Figure 6A:
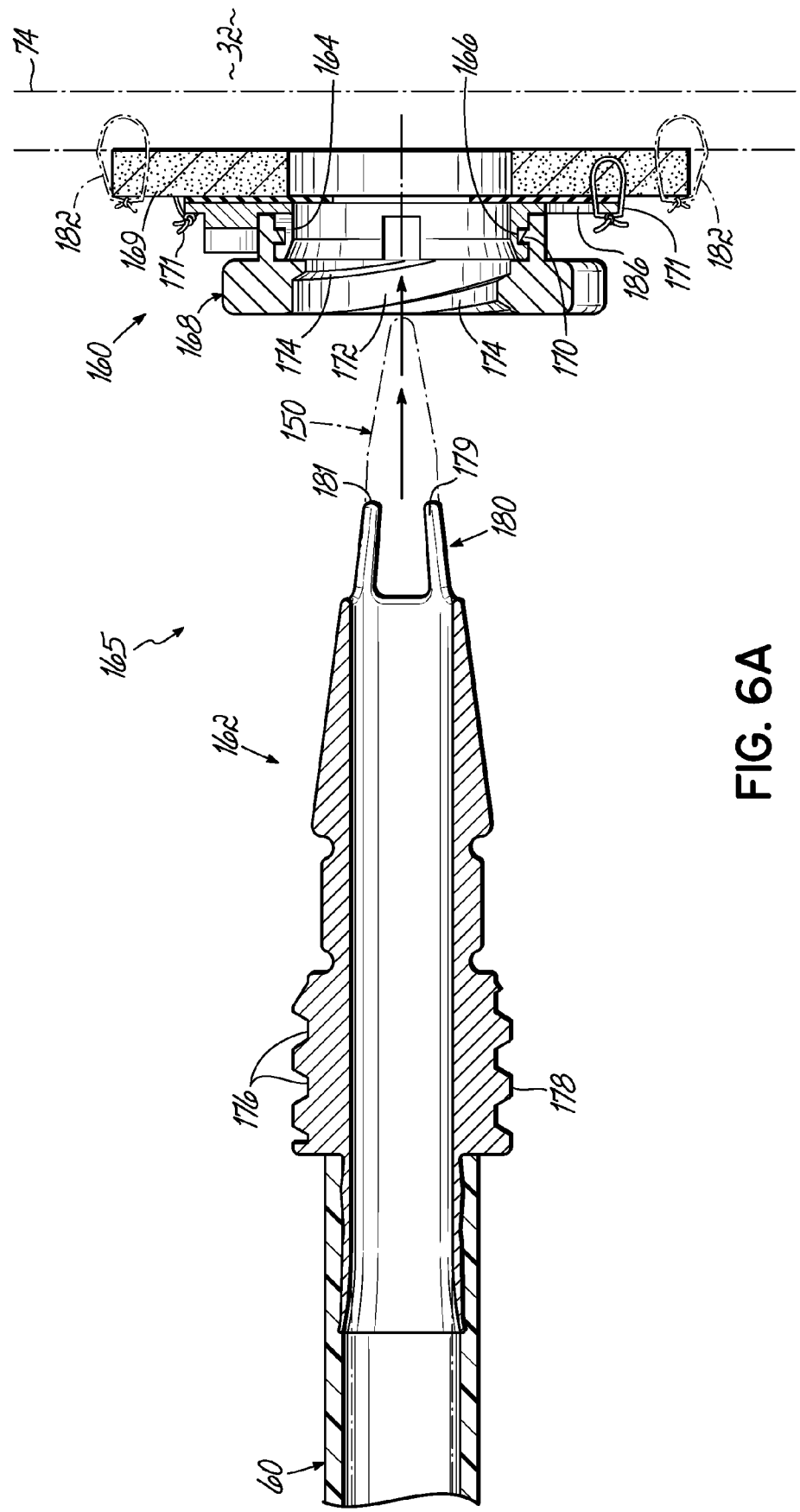
FIGS. 6A and 6B are cross-sectional views illustrating the sequence of an exemplary method of inserting and securing the cannula and tip with the locking mechanism shown in FIG. 5A into the heart of the patient.
Figure 6B:
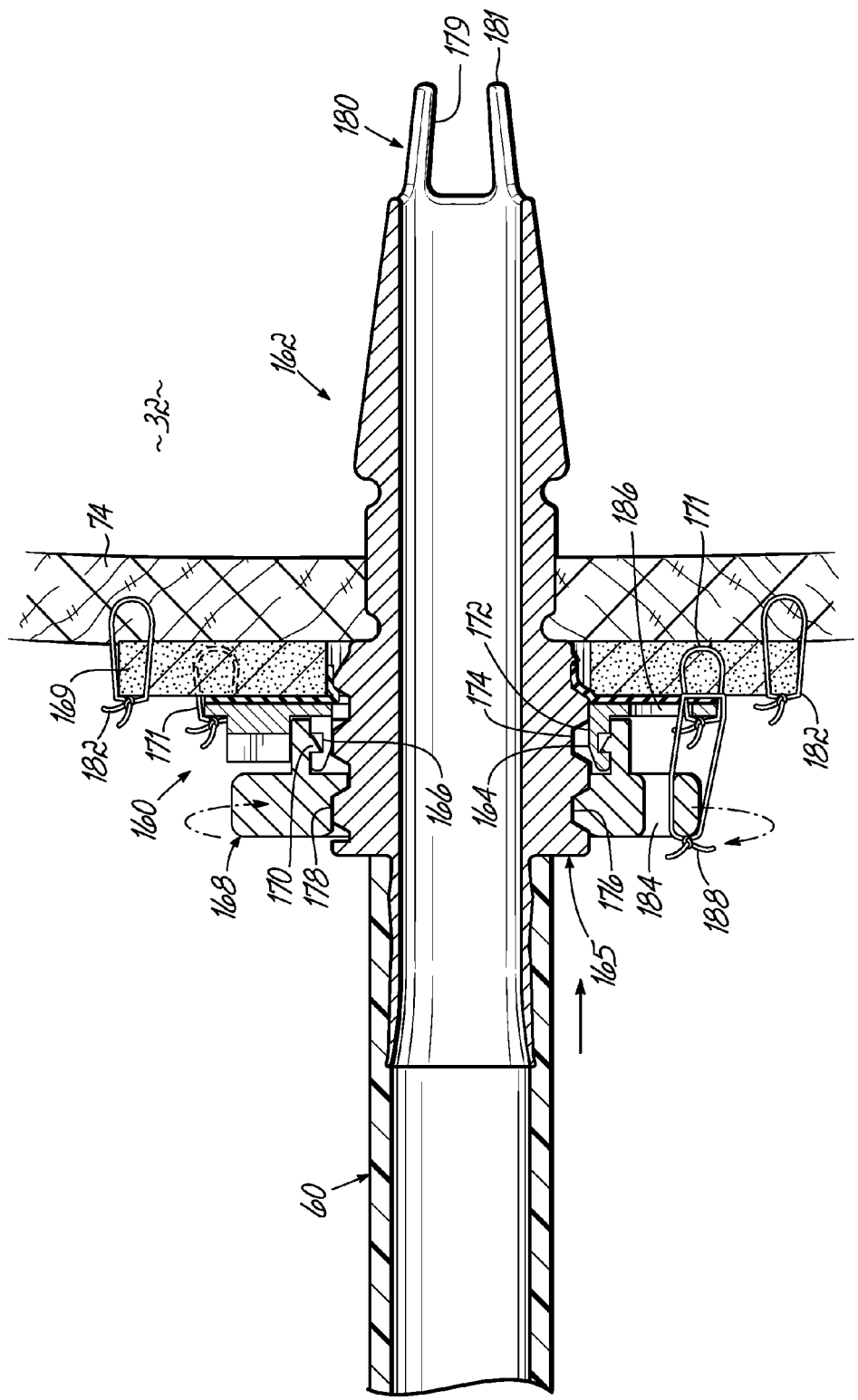

Use of the tip 162 and the sewing ring 160 is described with reference to FIGS. 6A and 6B. While the illustrative embodiment is shown with only the cutting obturator tip 150, in phantom, it would be understood that this is for clarity only. Indeed, the delivery system 130 of FIG. 3A or any other suitable delivery system design may be used with the illustrative procedure. Again, and prior to the procedure in FIG. 6A, the physician has secured the sewing ring 160 to the inflow access site 72, for example, by tying off one or more sutures 182, which for illustrative purposes, is located at the apex 74 of the heart 22 (FIG. 1). The physician then directs the tip 162, with the inflow cannula 60, through the sewing ring 160 and the apex 74 while the locking mechanism 165 is in a first locking state and as shown in FIG. 6A. Once the tip 162 is properly positioned through the apex 74 and with respect to the sewing ring 160, the physician may transition the locking mechanism 165 to the second locking state by rotating the threaded nut 168, for example, in the clockwise direction. This transition by rotation causes the first locking element, i.e., the continuous thread 174 of the threaded nut 168, to engage the second locking element, i.e., the threads 176 on the outer surface 178 of the tip 162. Clockwise rotation of the threaded nut 168 would, therefore, secure the tip 162 to the sewing ring 160 in at least a first position. Further advancement of the tip 162 into the left ventricle 32 to at least a second position may be accomplished by further rotation of the locking nut 168; counter-clockwise of the threaded nut 168 would retract the tip 162 from the left ventricle 32 to at least a third position with respect to the sewing ring 160. Various positions of the tip 162 with respect to the sewing ring 160 are thus possible and should not be limited to the discrete positions that are specifically shown. While not shown, the physician may monitor the tip depth within the left ventricle 32 by remote visualization, as described previously.

Once a cannula position, e.g., a selected tip depth, is achieved, the physician may further secure the relative positions of the threaded nut 168 and the sewing ring 160 to retain the selected tip depth with a third locking element 188. In this particular illustrative embodiment, the threaded nut 168 includes a plurality of through holes 184 positioned circumferentially around the nut 168. The molded body 164 of the sewing ring 160 includes a corresponding plurality of holes 186. As best shown in FIG. 6B, the physician may thread a suture strand 188 through the tissue comprising the apex 74 and two aligned holes 184, 186 (one from the plurality of circumferential holes 184 of the threaded nut 168 and one from the plurality of holes 186 of the molded body 164) to further secure and resist undesired motion post-operation.

Figure 7A:
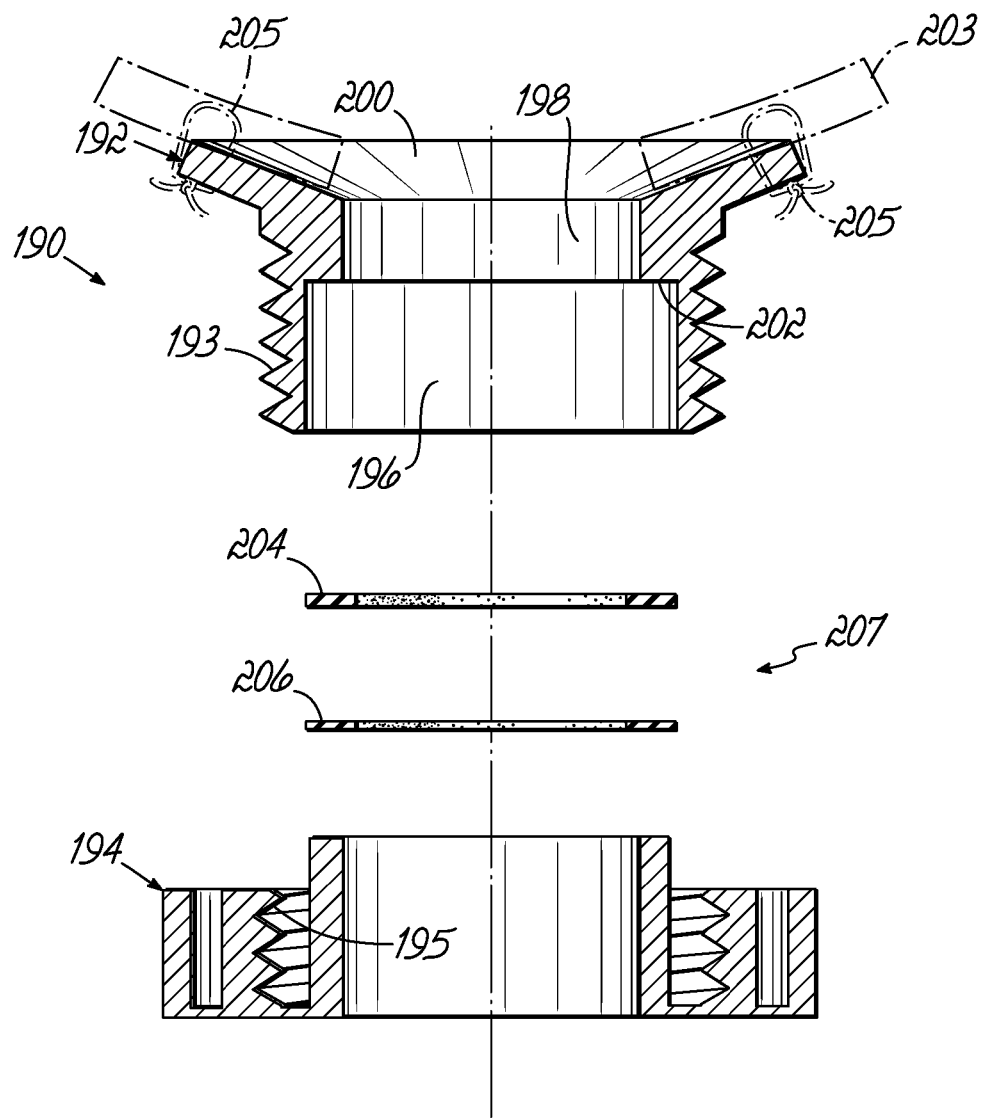
FIG. 7A is a exploded view of a tissue attachment ring for use with a cannula tip in accordance with yet another embodiment of the present invention.
Figure 7B:
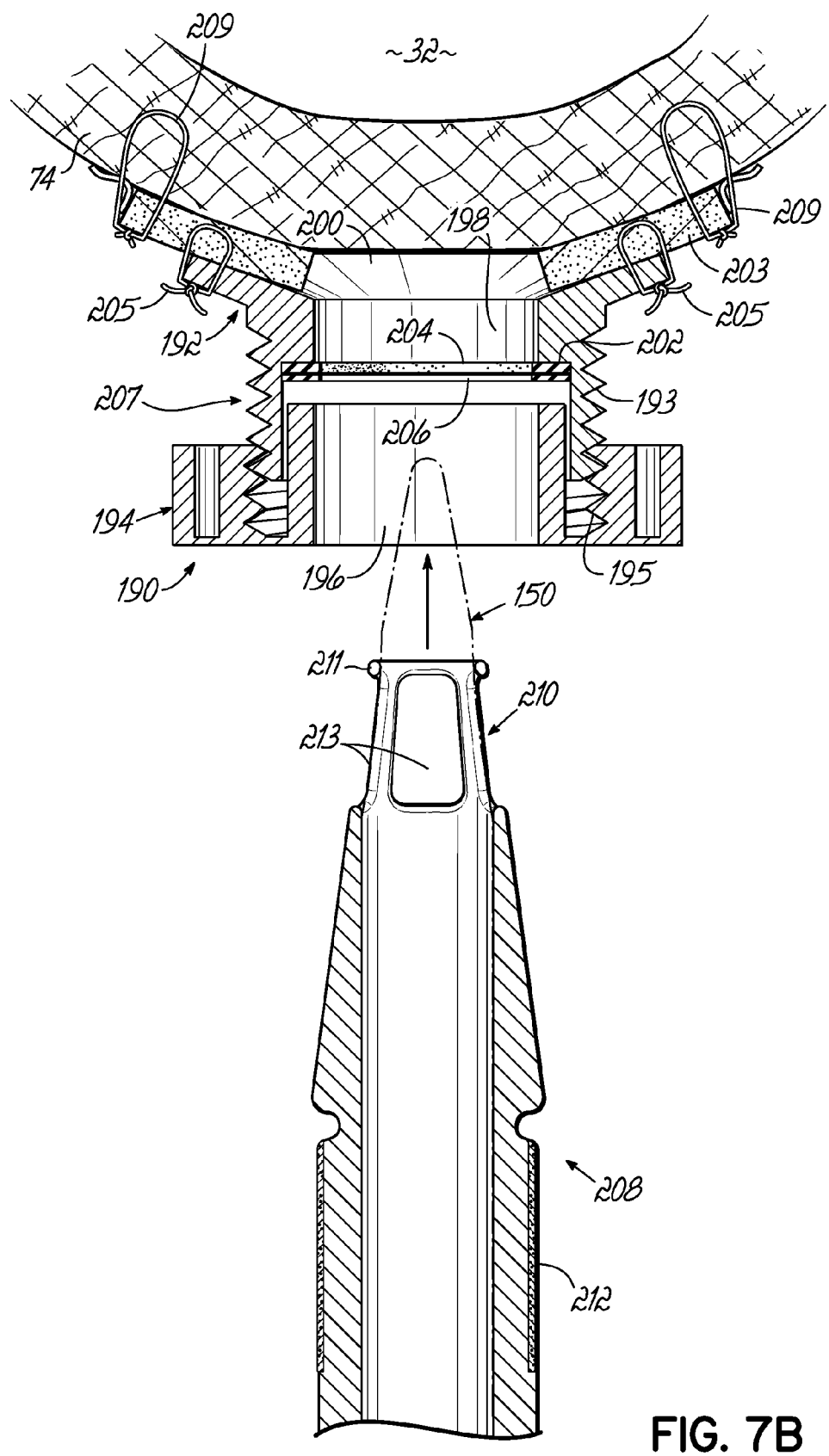
FIGS. 7B and 7C are cross-sectional views illustrating the sequence of an exemplary method of inserting and securing a cannula and tip with another embodiment of a locking mechanism to the heart with the tissue attachment ring of FIG. 7A.
Figure 7C:
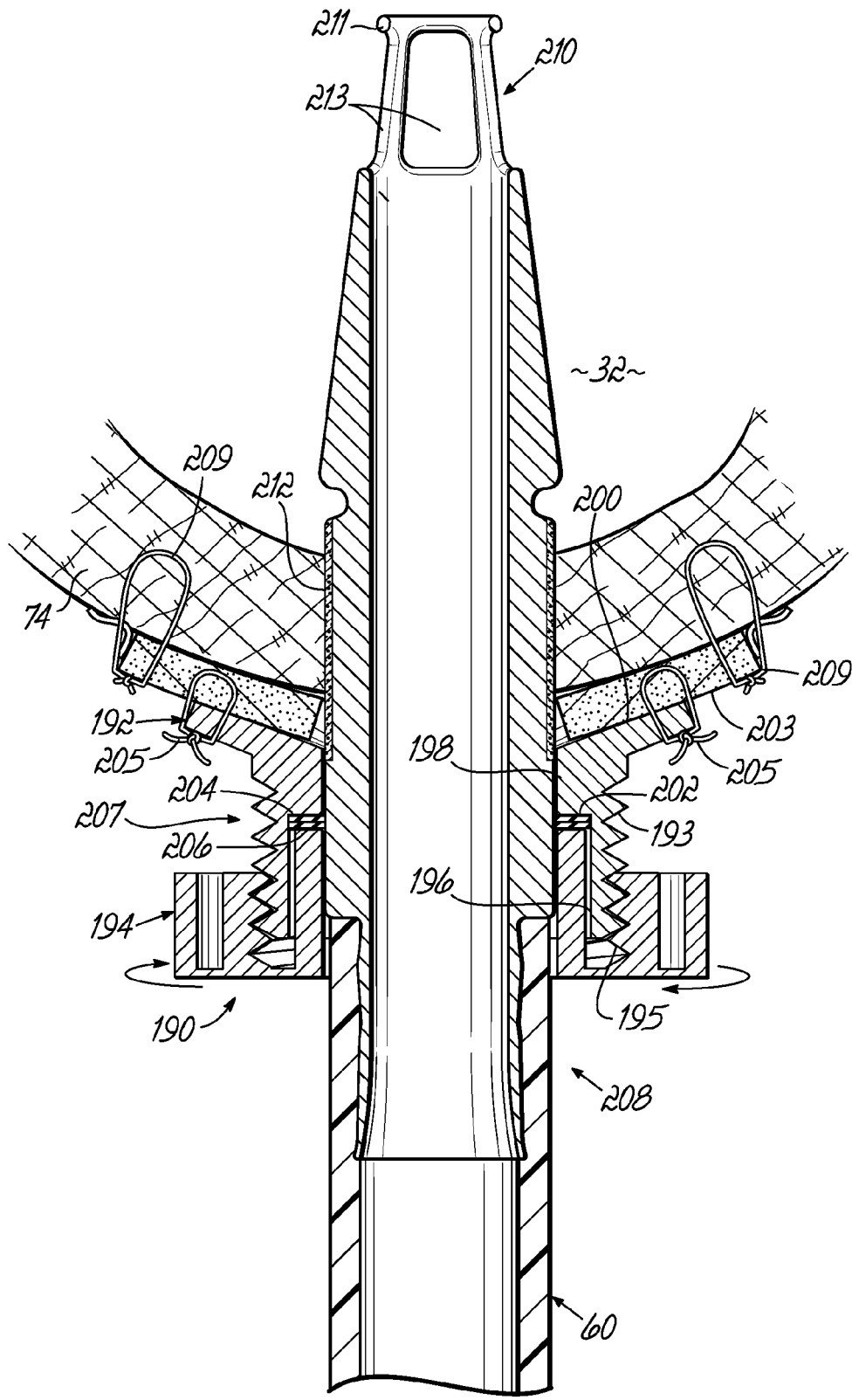

FIGS. 7A-7C illustrate yet another embodiment of the present invention in which a tissue attachment ring 190 is configured to be sutured (i.e., a sewing ring) at a tissue, for example, the apex 74 (FIG. 1). The sewing ring 190 includes first and second portions 192, 194 that are shown with outer and inner threaded surfaces 193, 195, respectively. The first portion 192 has a proximal lumen 196, a smaller diameter medial lumen 198, and a flaring distal lumen 200. A shelf 202 is formed between the larger proximal lumen 196 and the smaller medial lumen 198.

Two washers 204, 206 are captured between the first and second portions 192, 194 when assembled. The distally-positioned washer 204 (that is a locking mechanism 207 having a single locking element 204) may be constructed from silicone for providing a seal with a cannula tip 208 (FIG. 7B) and is generally thicker than the proximally-positioned wafer 206, which may be constructed from TEFLON for smooth rotation between the first and second portions 192, 194. A tissue in-growth band 203 is coupled to the flaring distal lumen 200 via one or more sutures 205, as described previously.

As shown in FIG. 7B, the physician positions the first portion 192 of the sewing ring 190 on an outer surface of the apex 74 such that the tissue in-growth band 203 resides against the tissue comprising the apex 74. The tissue in-growth band, with the first portion 192, is then secured to the apex 74 with one or more sutures 209. The second portion 194 is then threadably coupled, at least partially, to the first portion 192 and prepared to receive the cannula tip 208 with the delivery system 130 (FIG. 2A) and the cutting obturator tip 150 positioned therethrough.

In FIG. 7C, the cannula tip 208 is advanced through the sewing ring 190 such that the cutting blades 152 (FIG. 2A) cut the tissue of the apex 74 and the tip 208 enters the left ventricle 32. The particular illustrated cannula tip 208 includes a distal cage 210 with a distal ring 211 and a plurality of openings 213, and a smooth outer surface 212 that is located proximal to the distal cage 210. As the cannula tip 208 enters the medial lumen 198 of the first portion 192, the distally-positioned washer 204, being in a relaxed, first locking state, forms a fluid-tight seal about the cannula tip 208 while allowing the cannula tip 208 to move relative to the sewing ring 190. Once the cannula tip 208 is positioned as desired, as determined by remote visualization or another method, the physician then further threadably couples the second portion 194 to the first portion 192. With continued threaded coupling, the second portion 194 captures and compresses the distally-positioned washer 204 at the shelf 202, which forms a frictional fit between locking mechanism 207 and the cannula tip 208. The washer compression decreases the inner diameter of the distally-positioned washer 204, transitions the locking mechanism 207 to a compressed, second locking state, that locks or otherwise secures, the position of the tip 208.

Figure 8A:
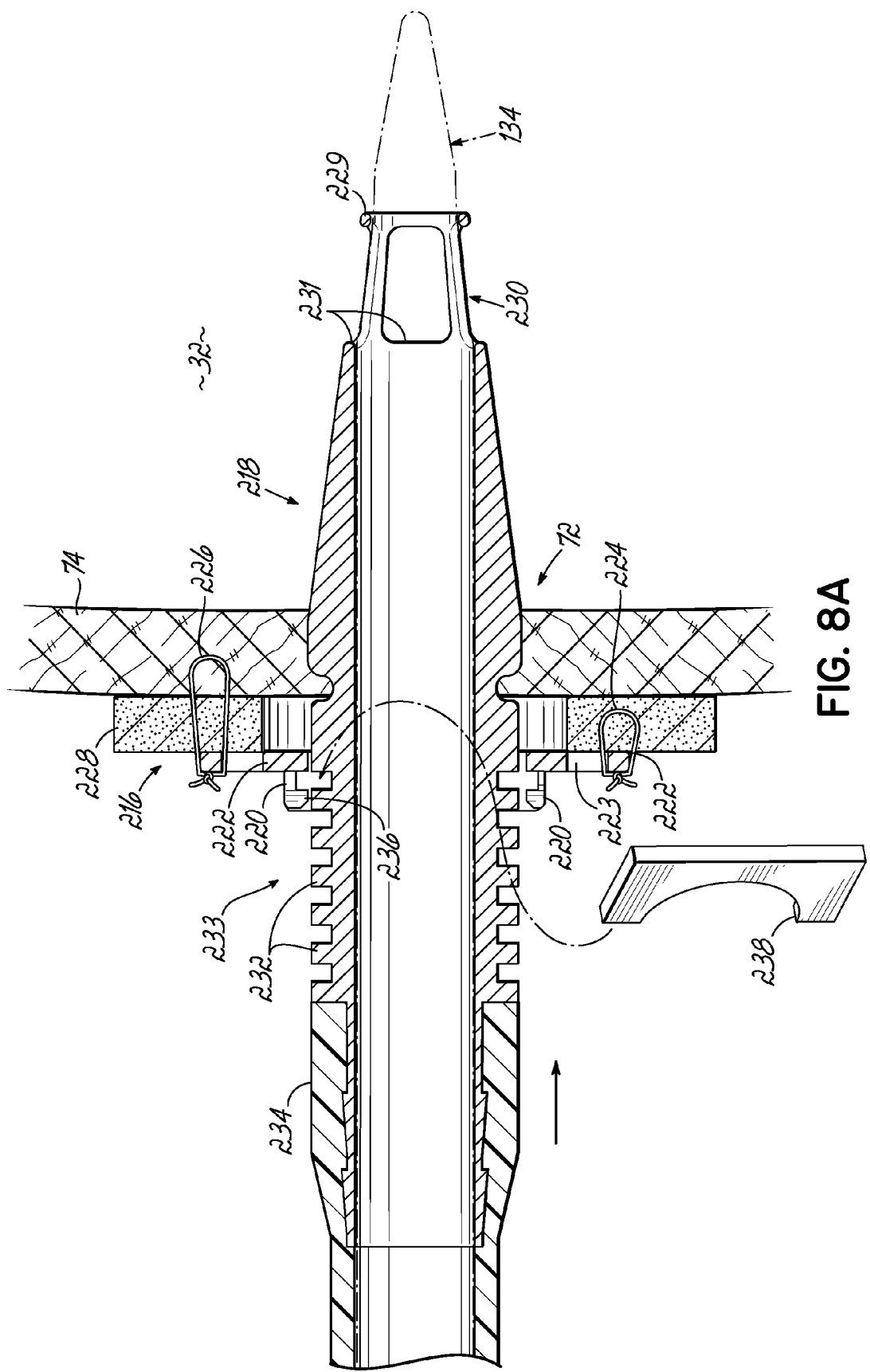
FIGS. 8A and 8B are cross-sectional views illustrating the sequence of a method of inserting and securing a cannula tip to a tissue attachment ring with a locking mechanism in accordance with another embodiment of the present invention.
Figure 8B:
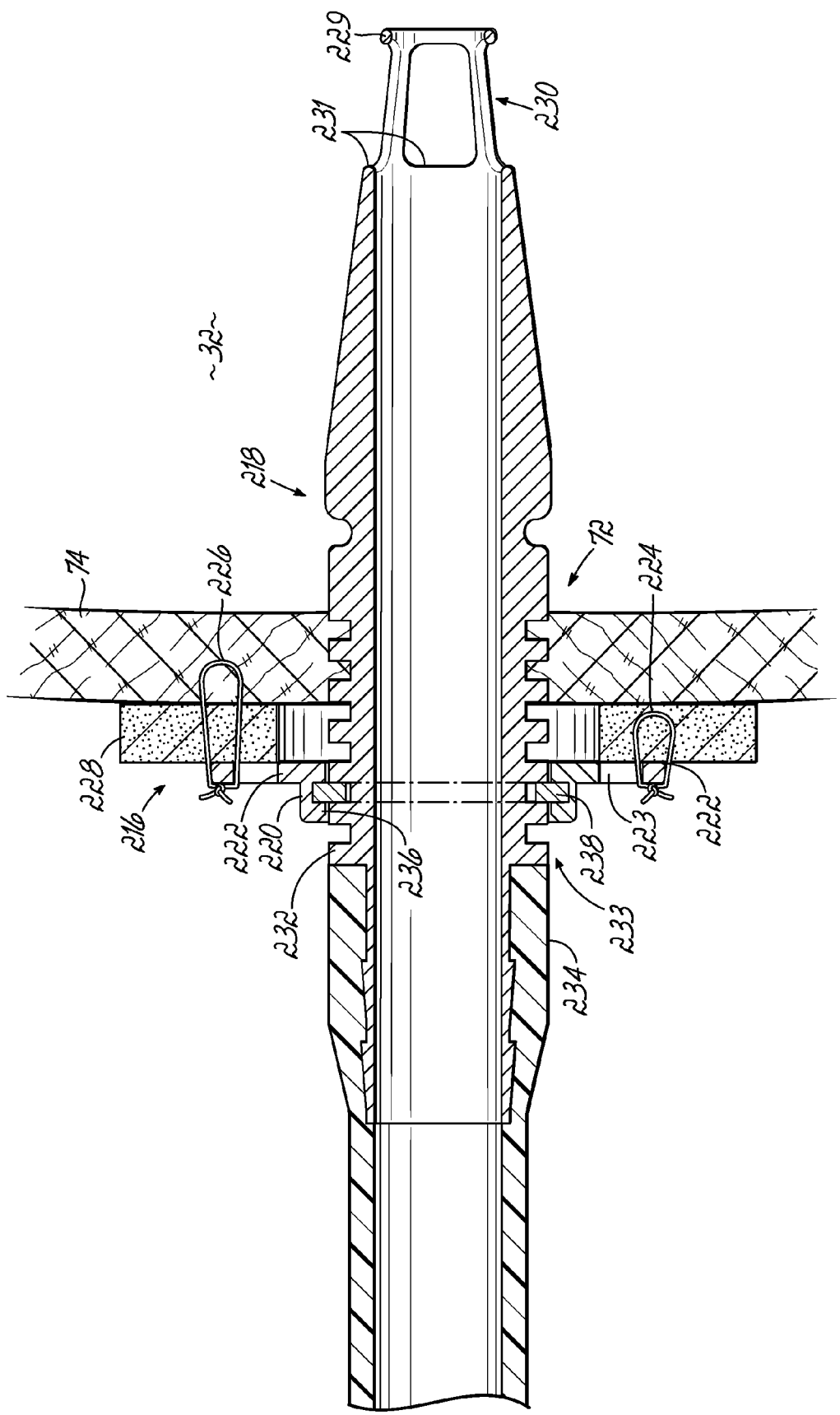

FIGS. 8A and 8B illustrate still another embodiment of a surgical cannula system including a tissue attachment ring 216 and a cannula tip 218. Again, the embodiment is illustrated with only the obturator tip 132 of the delivery system 130 (FIG. 3A); however, it is understood that the delivery system 130 (FIG. 3A) or any other suitable delivery system design may be used as desired. The tissue attachment ring 216, is secured by at least one suture 266 and may thus be referred to as a sewing ring. The sewing ring 216 includes a molded body 220 with a distally-positioned, radially-extending band 222 having a plurality of radial ribs 223 for attaching one or more sutures 224, 226. A tissue in-growth band 228 is coupled to a distal end surface of the radially-extending band 222 and may be constructed from a porous polymeric material, as described above.

The cannula tip 218 may be constructed as described above and generally includes a distal cage 230 (with a distal ring 229 and a plurality of openings 231) and a locking element 232 of a locking mechanism 233, for example, a dentate surface 232, on its proximal outer surface 234.

As the cannula tip 218 is inserted through the sewing ring 216 and into the left ventricle 32, one of the teeth 232 may be aligned with another locking element 236 of the locking mechanism 233 located on the sewing ring 216, for example, an inwardly-directed tab extending inwardly from the molded body 220 of the sewing ring 216. Distal to the tab 236 is an opening that, with a space between adjacent ones of the teeth of the dentate surface 232, forms a gap that is sized and shaped to receive a third locking element 238 that is configured to facilitate the locking relationship between the locking elements 232, 236. More specifically, a C-clamp 238, as shown in FIG. 8B, secures the position of the cannula tip 218 with respect to the sewing ring 216. Once the C-clamp 238 is inserted into the gap, the cannula tip 218 is secured with respect to the sewing ring 216; removing the C-clamp 238 allows the cannula tip 218 to move with respect to the sewing ring 216.

Figure 9A:
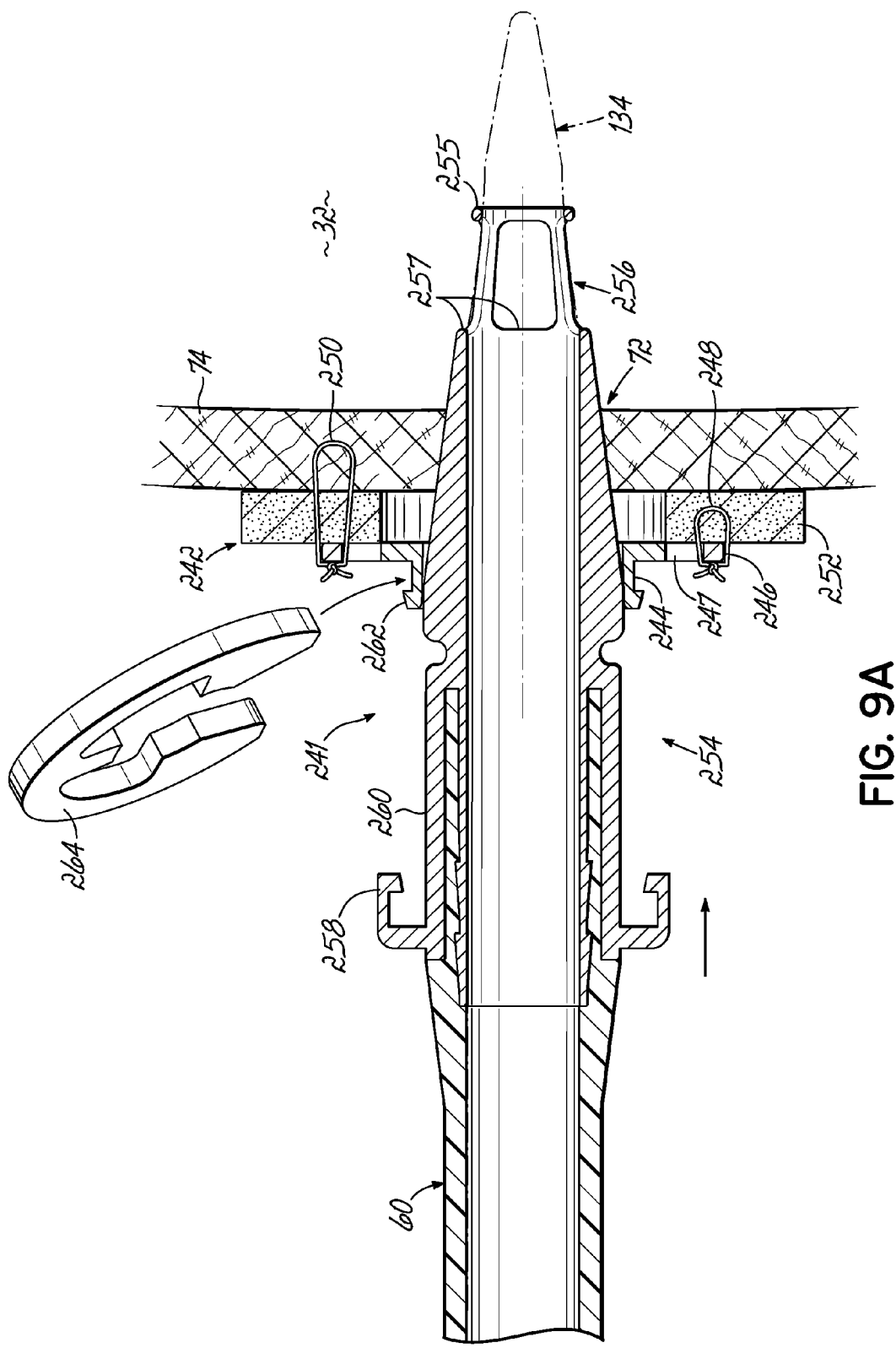
FIGS. 9A and 9B are cross-sectional views illustrating the sequence of a method of inserting and securing a cannula tip to a tissue attachment ring with a locking mechanism in accordance with another embodiment of the present invention.
Figure 9B:
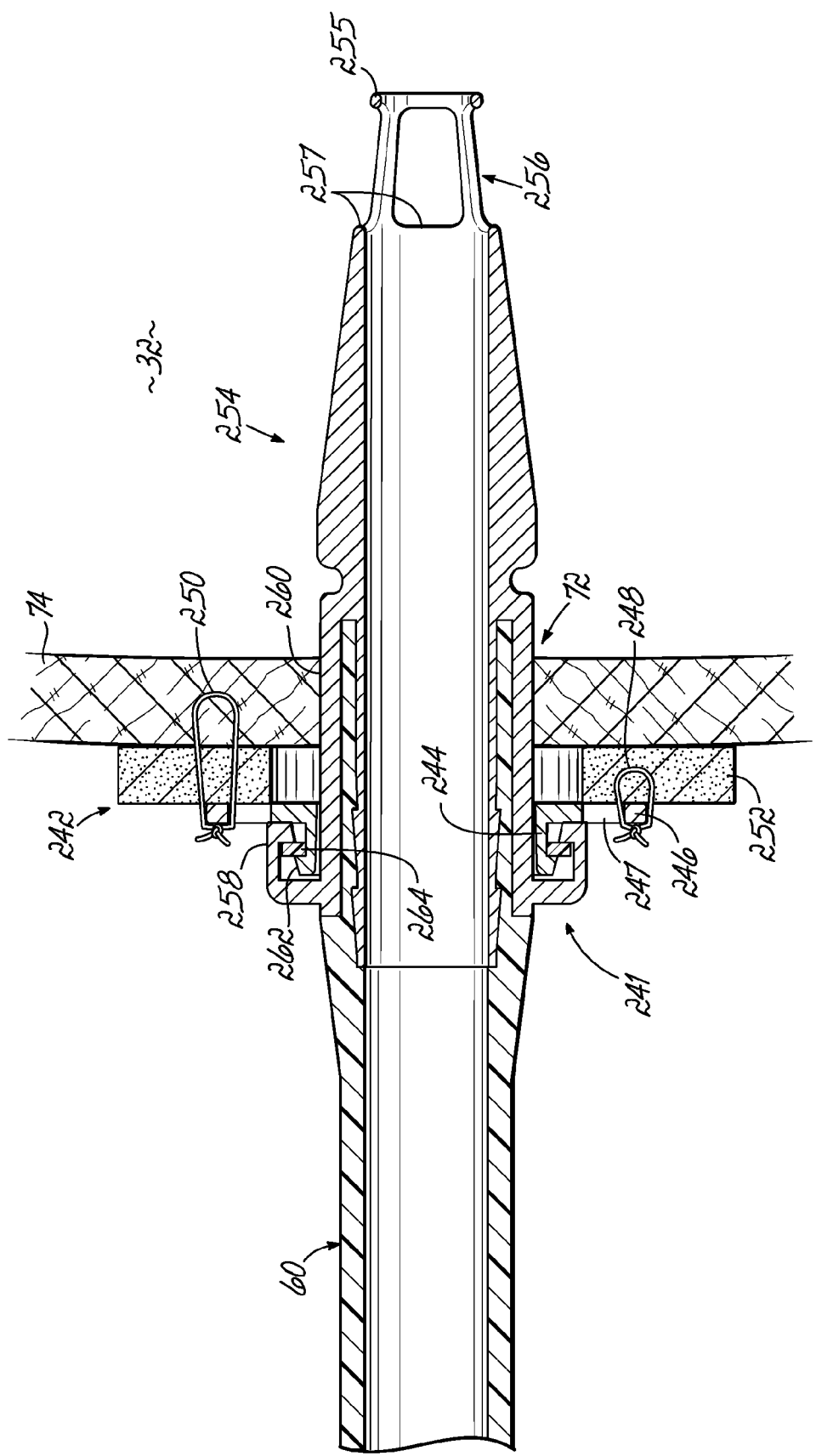

FIGS. 9A and 9B illustrate yet another embodiment of a locking mechanism 241 for a surgical cannula system. Again, the embodiment is illustrated with only the obturator tip 134 of the delivery system 130 (FIG. 3A). The tissue attachment ring 242 includes a molded body 244 with a distally-positioned, radially-extending band 246 and having a plurality of ribs 247 for attaching one or more sutures 248, 250 and may thus be referred to as a sewing ring. A tissue in-growth band 252 is coupled to a distal end surface of the radially-extending band 246 and may be constructed from a porous polymeric material, as described above.

The cannula tip 254 may be constructed as described above and generally includes a distal cage 256 (with a distal ring 255 and a plurality of openings 257) and radially-extending arms 258 on its proximal outer surface 260. In this embodiment, the locking mechanism 241 includes a space formed between a locking element 258 on the cannula tip 254 and another locking element 262 on the sewing ring 242. As is shown, the locking element of the cannula tip 254 includes radially-extending arms and the locking element 262 of the sewing ring 242 includes an outwardly-directed tab extending away from the molded body 244 of the sewing ring 242. A third locking element 264 then facilitates the locking relationship between the radially-extending arms 285 and the outwardly-directed tab 262. Particularly, the space created between the radially-extending arms 285 and the outwardly-directed arm 284 receives an E-ring 264, which secures the cannula tip 254 to the sewing ring 242.

Figure 10A:
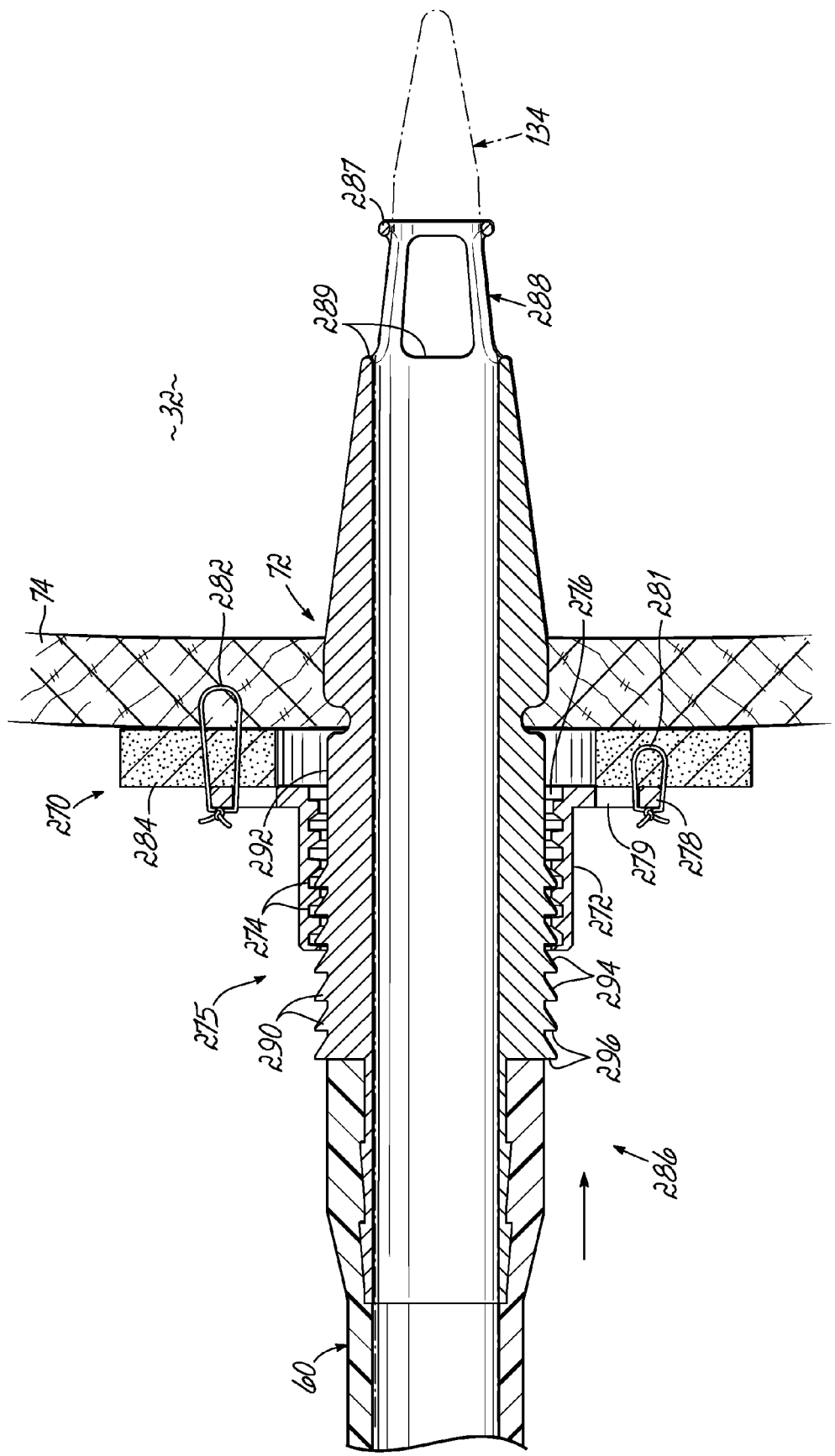
FIGS. 10A and 10B are cross-sectional views illustrating the sequence of a method of inserting and securing a cannula tip with a tissue attachment ring with a locking mechanism in accordance with another embodiment of the present invention.
Figure 10B:
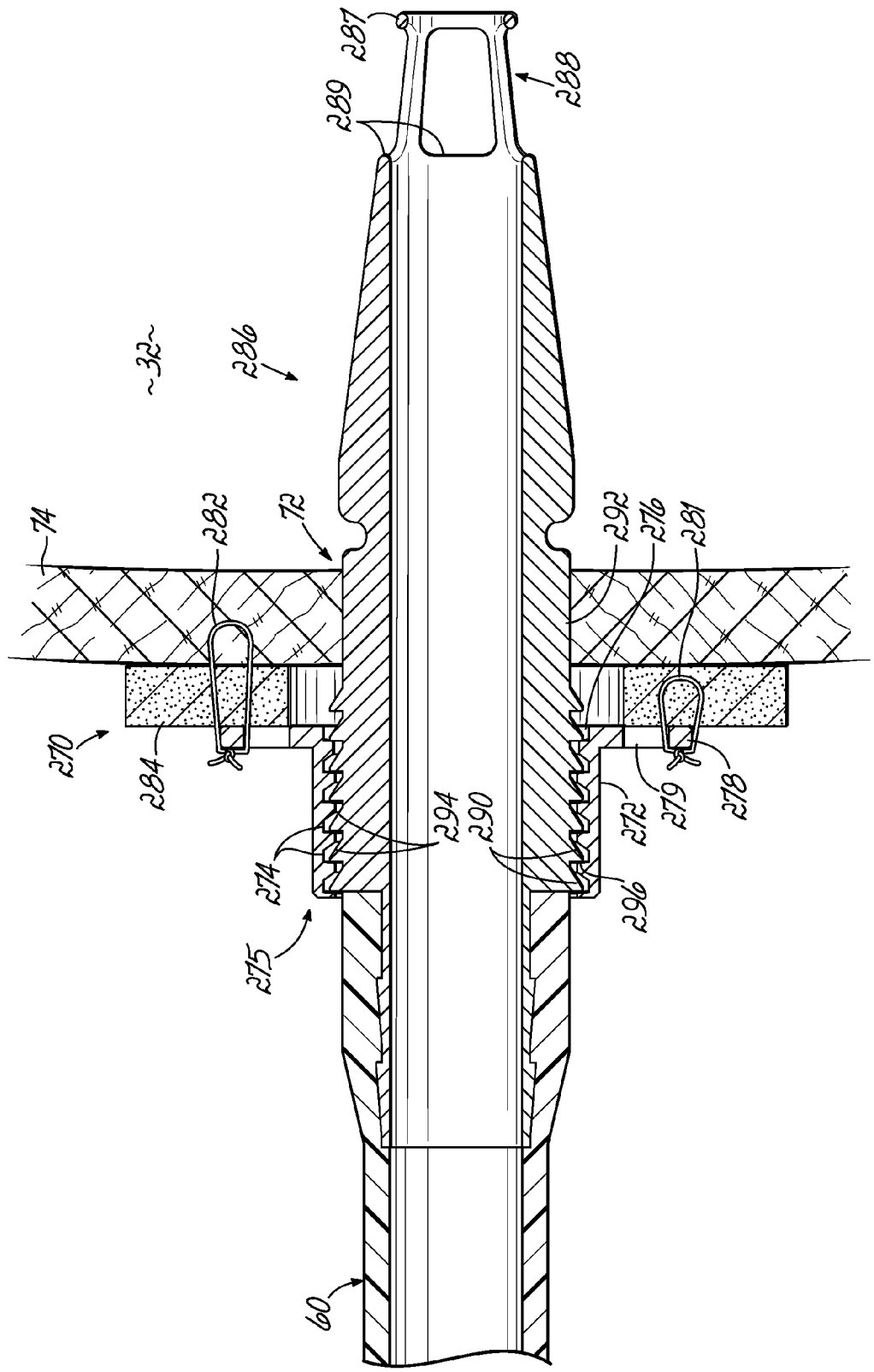

Yet another embodiment of the present invention is illustrated and described with reference to FIGS. 10A and 10B. Again, for convenience of illustration, only the obturator tip 134 of the delivery system 130 (FIG. 3A) is shown. In FIG. 10A, the tissue attachment ring 270 includes a molded body 272 having a first locking element 274 of a locking mechanism 275. The first locking element 274, may include, for example, a plurality of annular grooves along an inner surface of the lumen 276. The molded body 272 further includes a distally-positioned, radially-extending ring 278 having a plurality of ribs 279 for attaching one or more sutures 281, 282. A tissue in-growth band 284 is coupled to a distal end surface of the radially-extending ring 278 and may be constructed from a porous polymeric material, as described above.

The cannula tip 286 may be constructed as described above and includes a distal cage 288 (with a distal ring 287 and a plurality of openings 289) and a second locking element 290 that is configured to cooperate with the first locking element 275 to secure a position of the cannula tip 286 with respect to the tissue attachment ring 270. The second locking element 290 may be a plurality of angled teeth 290 on its proximal, outer surface 292, wherein each tooth 290 of the plurality includes an angled distal surface 294 and a planar proximal surface 296, that is, in a manner that is similar ratchet.

As the physician advances the cannula tip 286 through the sewing ring 270 and into the left ventricle 32, the plurality of angled teeth 290 engage the plurality of grooves 274 within the molded body 272, such as in a one-way ratcheting motion to a first position. As a result, the locking mechanism 275 may be transitioned between a first locking state for advancing the cannula tip 286 to another position that is further located in the left ventricle 32; however, the planar proximal surfaces 296 resist retraction of the cannula tip 286 from the sewing ring 270 and maintains the cannula tip 286 in the second locking state that resists movement of the cannula tip 286 back into the first locked position.

Figure 11:
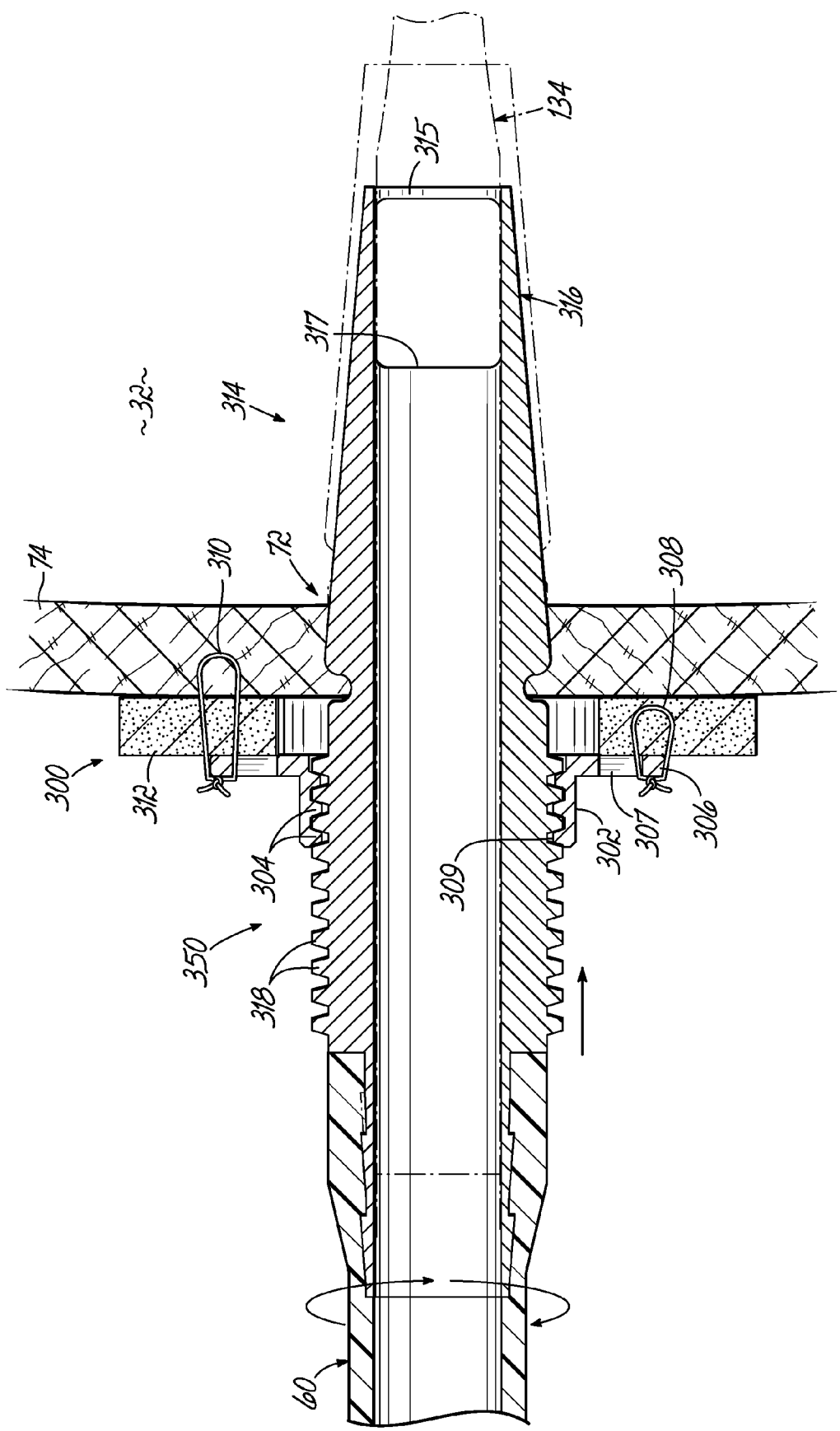
FIG. 11 is a cross-sectional view illustrating one exemplary method of securing a cannula tip and a tissue attachment ring with a locking mechanism in accordance with another embodiment of the present invention.

FIG. 11 illustrates another alternate embodiment of the present invention. Again, the embodiment is illustrated with only the obturator tip 134 of the delivery system 130 (FIG. 3A). The sewing ring 300 includes a molded body 302 having a first locking element 304 of the locking mechanism 305, wherein the first locking element 304 of the illustrative embodiment is an inner threaded surface provided on a wall 309 defining the lumen. The molded body 302 further includes a distally-positioned, radially-extending ring 306 having a plurality of ribs 307 for attaching one or more sutures 308, 310. A tissue in-growth band 312 is coupled to a distal end surface of the radially-extending ring 306 and may be constructed from a porous polymeric material, as described above.

The cannula tip 314 may be constructed as described above and includes a distal cage 316 (with a distal ring 315 and a plurality of openings 317) and second locking element 318 that cooperates with the first locking element 304 to secure at least one position of the cannula tip 314. Specifically, the first locking element includes a proximally-positioned, outer threaded surface that matches the inner threaded surface 304 of the molded body 302. The cannula tip 314 is directed into and threadably engages the sewing ring 300. As shown, rotating the cannula tip 314 clockwise advances the cannula tip 314 with respect to the sewing ring 300 to another position and increases the tip depth (shown in phantom) while counter-clockwise rotation retracts the cannula tip 314 and decreases the tip depth.

FIGS. 12A-12E illustrate yet another embodiment of the present invention in use with the delivery system 130 of FIG. 3A. As shown, a tissue attachment ring 320 (again, configured to be attached to the biological tissue with one or more sutures 328) includes a molded body 322 having a distally-positioned, radially-extending ring 324. A plurality of ribs 325 extend between the molded body 322 and the ring 324 for attaching one or more sutures 326, 328. A tissue in-growth band 330 is coupled to a distal end surface of the radially-extending ring 324 and may be constructed from a porous polymeric material, as described above.

The cannula tip 332 may be constructed as described above and include a distal cage 334 with a distal ring 333 and a plurality of openings 335 therein. A cross-sectional dimension of an outer surface 336 of the cannula tip 332 is irregular. More specifically, as more clearly shown in FIGS. 12D and 12E, the cross-section is slightly oval, i.e., having major and minor axes illustrated as major and minor outer diameters 338, 340, respectively, where the major outer diameter 338 is greater than the minor outer diameter 340. Likewise, the cross-section of an inner surface 342 of the lumen 344 of the molded body 322 includes a similar irregularity, i.e., both major and minor axes that are illustrated by first and second diameters 346, 348, respectively.

Figure 12A:
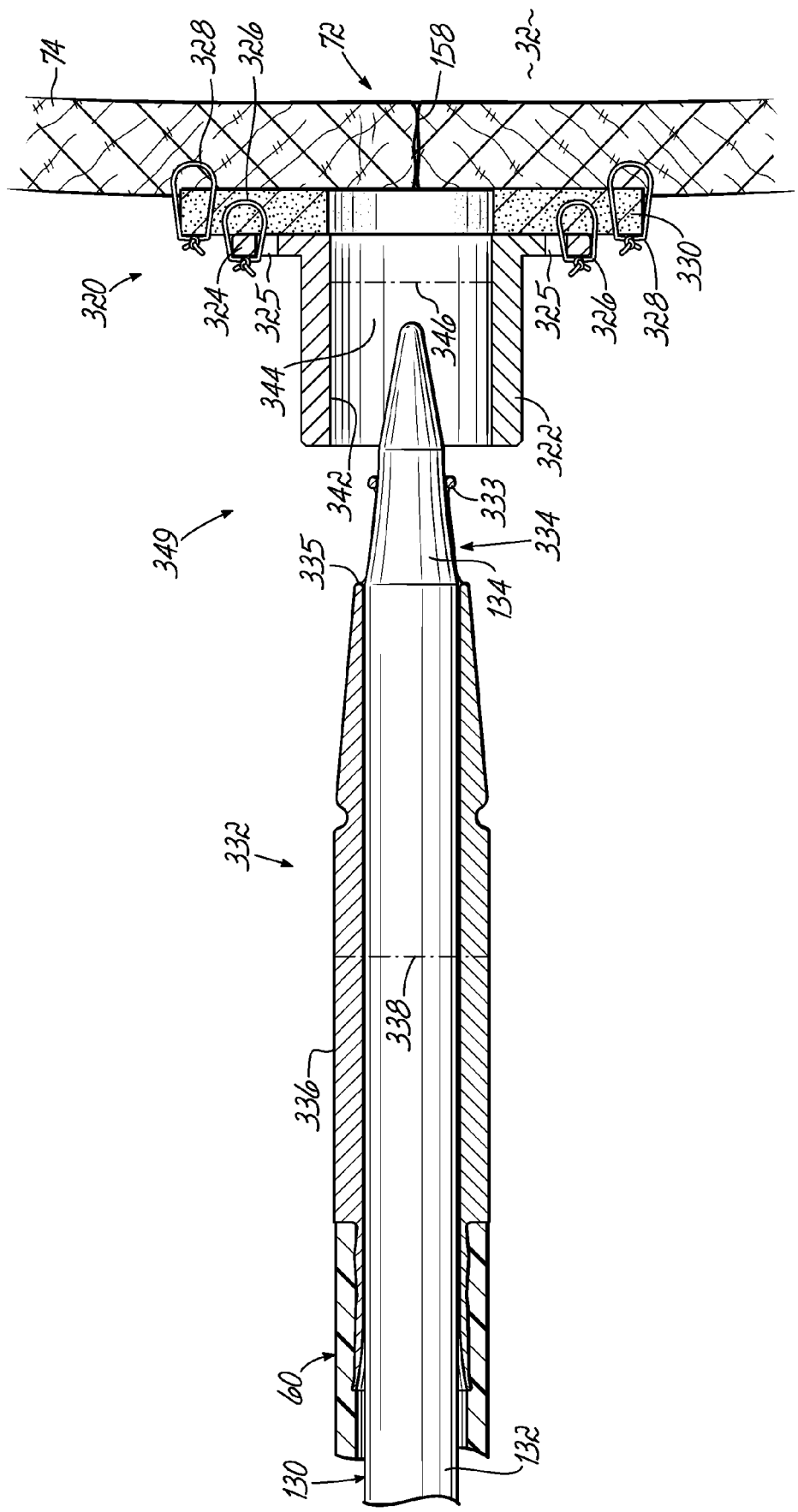
Figure 12B:
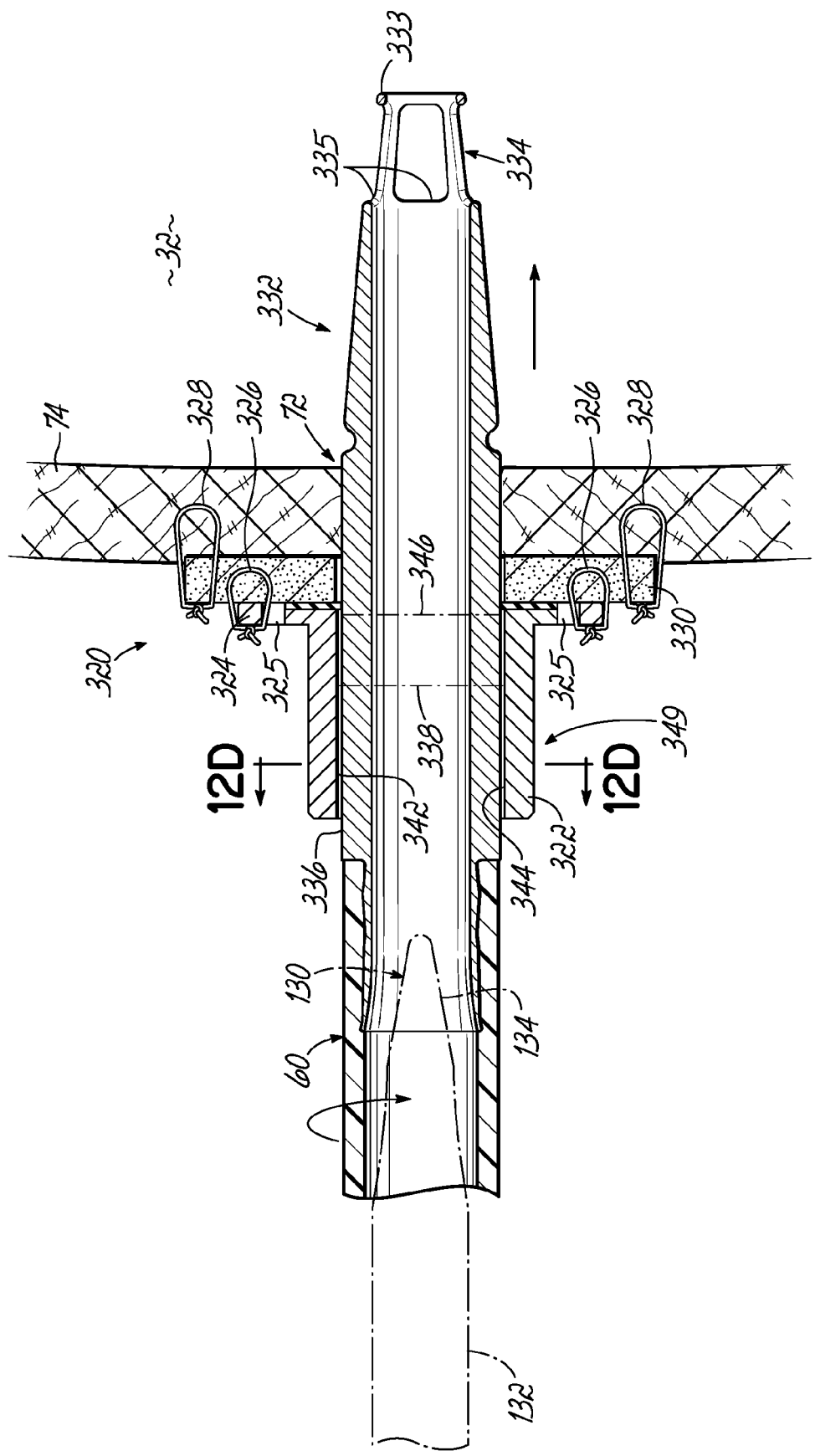

The locking mechanism 349 secures the cannula tip 332 to the sewing ring 320 by transitioning from a first locking state, as shown in FIG. 12B, and the corresponding cross-section in FIG. 12D, to a second locking state, shown in FIGS. 12C and 12E. In other words, the major outer diameter 338 of the cannula tip 332 is aligned with the first diameter 346 of the sewing ring 320. Consequently, the minor outer diameter 338 of the cannula tip 332 also aligns with the second diameter 348 of the sewing ring 320. In this arrangement, or locking state, there is sufficient clearance for the cannula tip 332 to be advanced into the lumen 344 of the molded body 322 to a desired position. Once the physician has properly advanced the cannula tip 332 into the left ventricle 32, the physician may rotate the cannula tip 332 within and with respect to the sewing ring 320. As shown in FIG. 12C, and the corresponding cross-section in FIG. 12E, rotation of the cannula tip 332 causes the major outer diameter 338 of the cannula tip 332 to move toward the second diameter 348 of the molded body 322. It would be readily understood that maximum frictional interference, and thus securement of the cannula tip 332, would occur approximately when the major outer diameter 338 of the cannula tip 332 is directly in alignment with the second diameter 348 of the molded body 322. Thus, once the physician has advanced the cannula tip 332 to a first position within the left ventricle 32 and with respect to the sewing ring 320, the physician may rotate the cannula tip 332, clockwise or counter-clockwise, by less than about 90° to a second locking state and secure the cannula tip 332. Release and repositioning of the cannula tip 332 may occur with rotation greater than 90° in the opposing direction, which again aligns the major outer diameter 338 with the first diameter 346. It would be readily appreciated that the position of the cannula tip 332 with respect to the sewing ring 320 may vary greatly between a distal boundary position and a proximal boundary position.

Figure 13A:
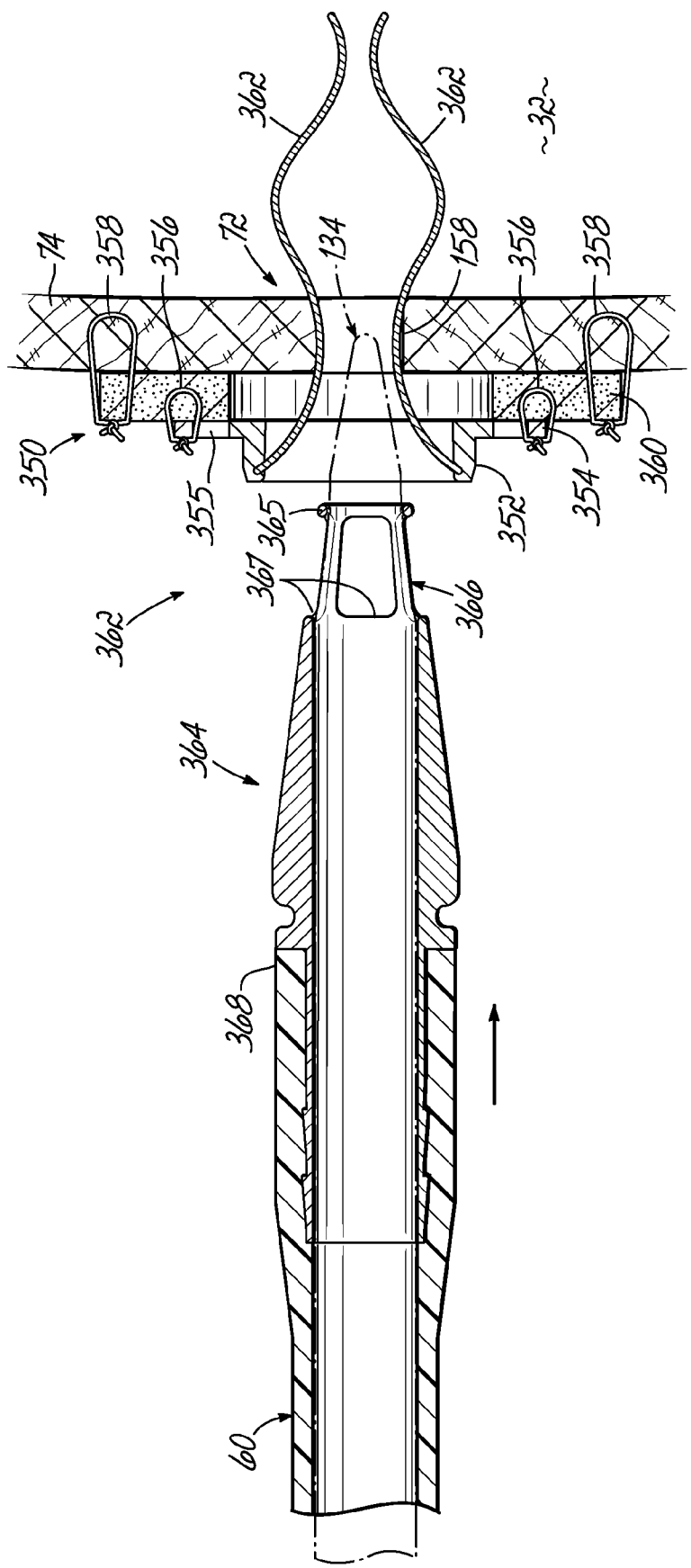
FIGS. 13A and 13B are cross-sectional views illustrating the sequence of a method of inserting and securing a cannula tip with a tissue attachment ring with a locking mechanism in accordance with another embodiment of the present invention, to the heart of a patient.
Figure 13B:
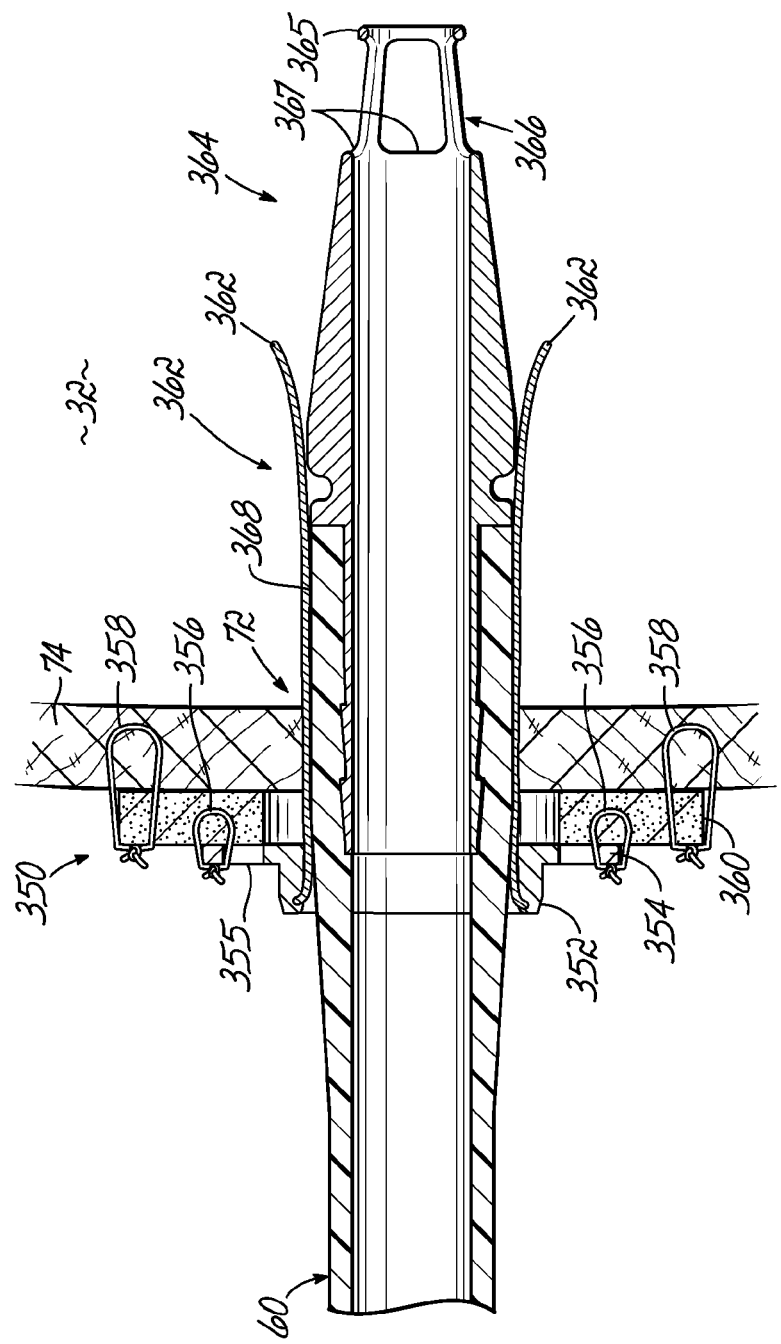
Figure 14A:
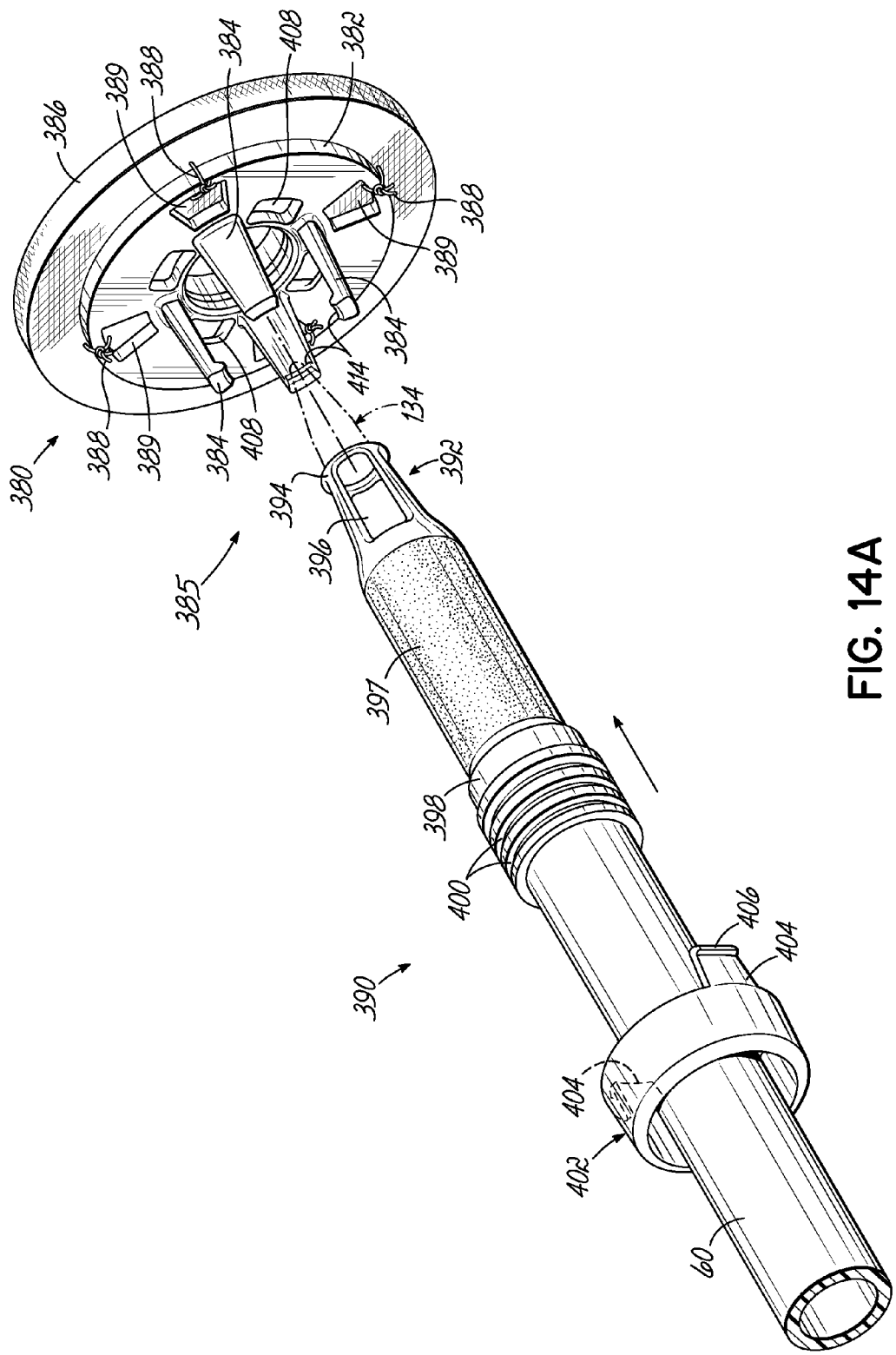
FIG. 14A is an exploded view of a cannula tip and a tissue attachment ring in accordance with another embodiment of the present invention.

Still another embodiment is described with reference to FIGS. 13A and 13B. As described previously, only the obturator tip 134 of the delivery system 130 (FIG. 3A) is shown for illustrative convenience. As shown, a tissue attachment ring 350 (again, illustrated specifically as a sewing ring) includes a molded body 352 having a distally-positioned, radially-extending ring 354 with a plurality of ribs 355 for attaching one or more sutures 356, 358. A tissue in-growth band 360 is coupled to a distal end surface of the radially-extending ring 354 and may be constructed from a porous polymeric material, as described above. The locking mechanism 362 of the illustrative embodiment is generally, operably coupled to an inner wall 363 of the molded body 352 and, specifically, includes one or more memory-shaped springs that may extend distally from the molded body 352, through the puncture wound 158, and into the left ventricle 32. The memory-shaped springs 362 may be constructed from a sheet of a superelastic material, electropolished to remove rough edges generated during the formation process, and then heated to a superelastic state.

The cannula tip 364 may be constructed as described above and include a distal cage 366 (with a distal ring 365 and a plurality of openings 367) and a smooth proximal surface 368. To secure the cannula tip 364 and actuate the locking mechanism 362, as the cannula tip 364 is advanced through the molded body 352, the memory-shaped springs 362 are biased from a first locking state (i.e., relaxed as shown in FIG. 13A) to a second locking state (i.e., straight shape as shown in FIG. 13B) that may be, for example, generally parallel to the longitudinal axis of the tip 364. This straightening of the memory-shaped springs 362 resists movement, proximally or distally, of the cannula tip 364. However, sufficient force applied to the cannula tip 364 overcomes this resistance and allows the physician to adjust the tip depth as desired. Accordingly, and depending on the biasing strength of the memory-shaped springs 362, the position of the cannula tip 364 with respect to the sewing ring 350 may vary greatly between a distal boundary position and a proximal boundary position or may be limited to one or more discrete positions.

With reference now to FIGS. 14A-15C, another embodiment of a tissue attachment ring 380 (specifically shown as a sewing ring) is described. More specifically, in FIGS. 14A-14C, the sewing ring 380 is shown and includes a ring portion 382 having a first locking element 384 of a locking mechanism 385, wherein the first locking element 384 is in the form of a plurality of prongs extending from the ring portion 382. A tissue in-growth band 386 is coupled to the ring portion 382 via one or more sutures 388 extending through one or more apertures 389.

The cannula tip 390 may include a distal cage 392 having a distal ring 394 and one or more apertures 396 as described previously. A proximal end 398 of the cannula tip 390 includes a second locking element 400 of the locking mechanism 385, wherein the second locking element 400 is in the form of one or more annular ridges 400 configured to be coupled to the prongs 384 of the sewing ring 380 as described below. While the particular illustrative embodiment includes multiple annular ridges 400 for providing multiple positions of the cannula tip 390 with respect to the sewing ring 380, it would be understood that only one annular ridge, and thus only one position of the cannula tip 390 with respect to the sewing ring 380 in a locking state, is necessary.

The cannula tip 390 may further include a portion 397 adapted to enable tissue ingrowth. The area 397 may include or be formed from a material suitable for promoting tissue ingrowth. For example, the portion 397 may be formed from a sintered material, or its outer surface may have a suitable coating or porous fabric (e.g., polyester) or other material for promoting tissue ingrowth. Tissue ingrowth in area 397 would be advantageous in that it will help in securing the cannula tip 390 to the tissue 74 (FIG. 15B) after implantation.

The particular embodiment further includes a third locking element 402 of the locking mechanism 385, e.g., a collar that is in sliding relationship with the cannula 60 and the cannula tip 390. The collar 402 includes one or more prongs 404, each having a radially-extending tab 406 that is configured to be received by an aperture 408 in the ring portion 382 of the sewing ring 380.

Figure 15A:
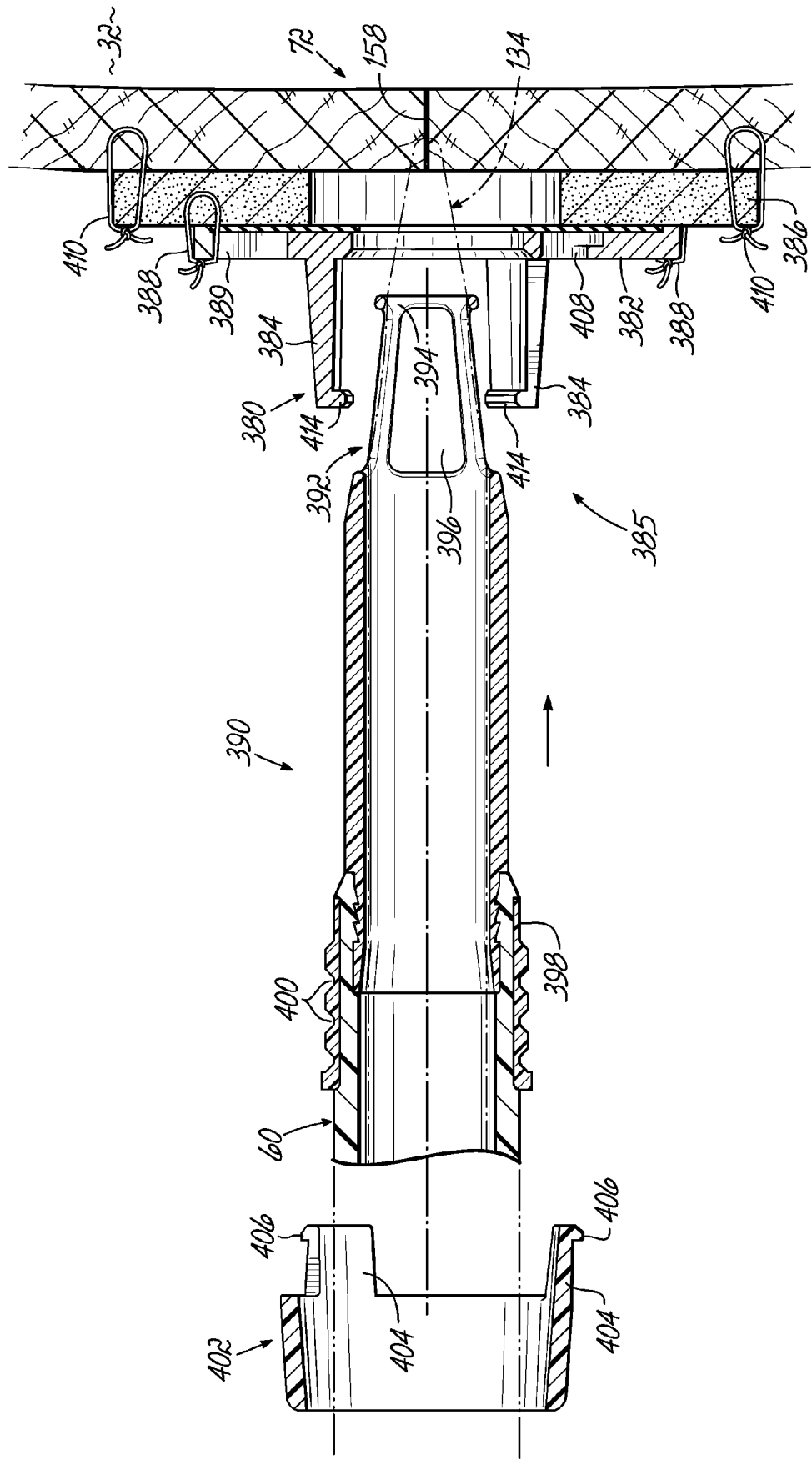
FIGS. 15A-15C are cross-sectional views illustrating the sequence of a method of inserting and securing the cannula tip to the tissue attachment ring of FIG. 14A and in accordance with another embodiment of the present invention.

Referring now to FIG. 15A, the sewing ring 380 has been coupled to the apex 74 by one or more sutures 388 extending through the apertures 389 of the ring portion 382 and at least partially into the tissue comprising the apex 74. The cannula 60 with the cannula tip 390 are then advanced to the sewing ring 380 with a delivery system 130 (FIG. 3A), where in FIG. 15A only the obturator tip 134 is shown.

Figure 15B:
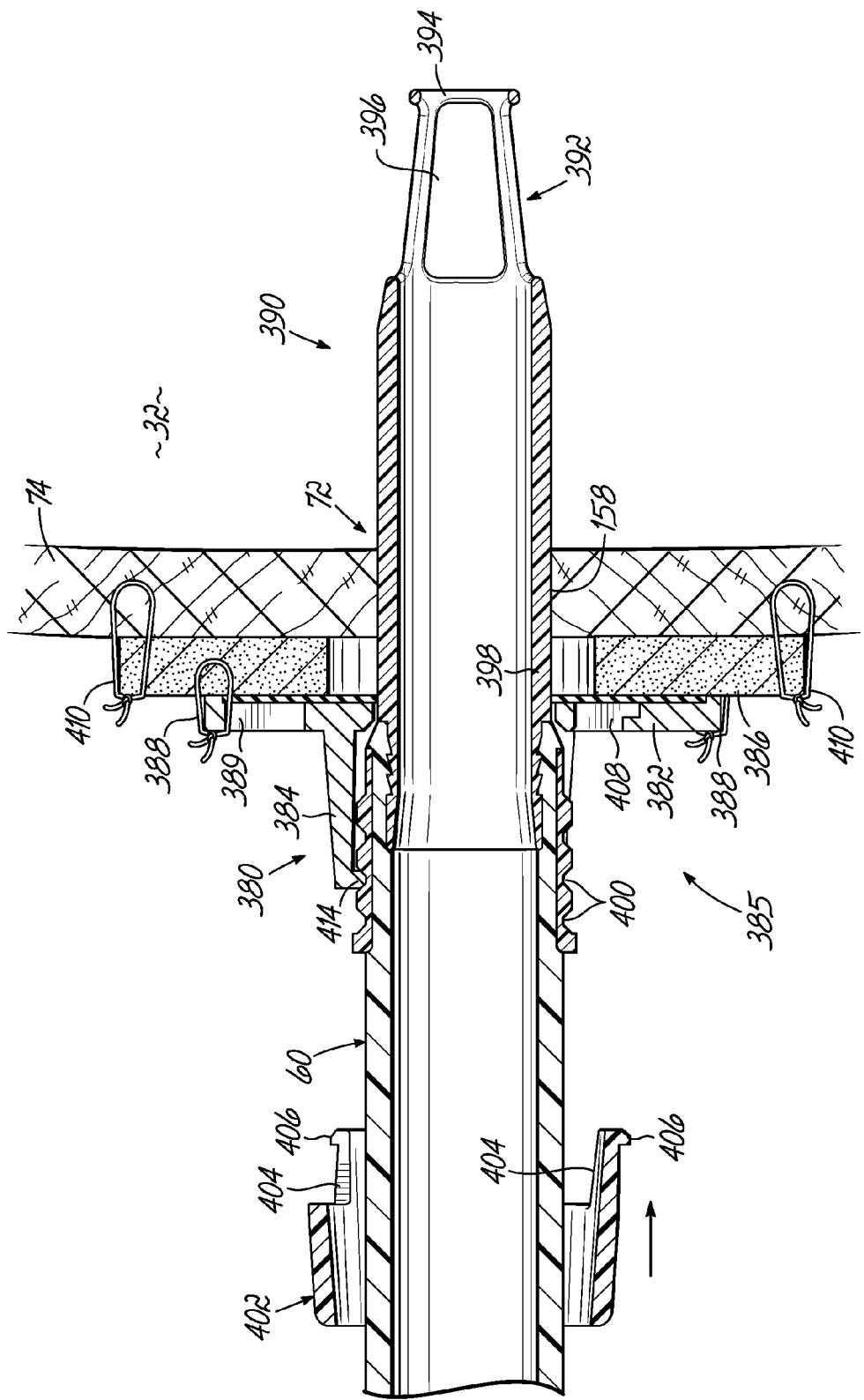

The obturator tip 134 is directed through the puncture wound 158 so that the cannula tip 390 enters the left ventricle 32. In FIG. 15B, the cannula tip 390 continues advancing into the sewing ring 380 until an inwardly-directed tab 414 on the prong 384 of the sewing ring 380 engages one of the annular ridges 400 in a first locking position. The depth of the cannula tip 390 within the left ventricle 32 may be selected, in part, on which annular ridge 400 the inwardly-directed tab 414 resides.

Figure 15C:
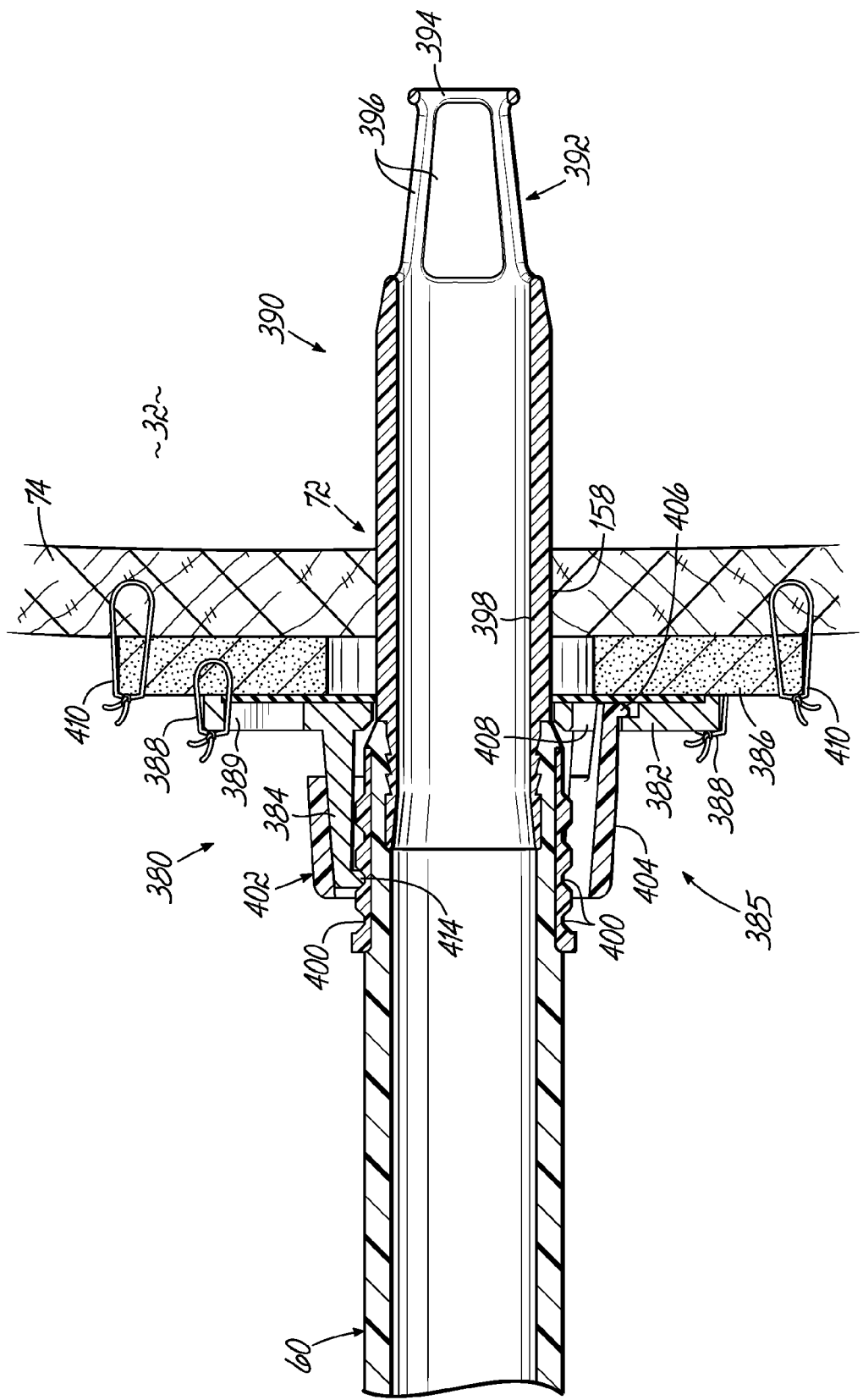

In FIG. 15C, the position of the cannula tip 390 with respect to the sewing ring 380 is further secured by sliding the collar 402 over the cannula 60 and the cannula tip 390 to engage the sewing ring 380. More specifically, the tabs 406 of the prongs 404 of the collar 402 extend through the apertures 408 of the sewing ring 380. The friction fit between the collar 402 and the outer proximal surface of the cannula tip 390 resists movement of the cannula tip 390 once the collar 402 is so engaged.

In still another embodiment, and as shown in FIGS. 16 and 17, rather than using the collar 402, the locking mechanism 425 of FIGS. 16 and 17 includes a third locking element 423 comprising an eyelet 424 attached to each of the plurality of prongs 420 extending from the ring portion 382 of the sewing ring 380. Each eyelet 424 includes an opening 426 through which a suture 428 is threaded. In use, after the cannula tip 390 is suitably positioned within the sewing ring 380, the suture 428 may be tightened and secured so as to draw the inwardly-directed tabs 422 of each prong 420 into one of the annular ridges 400.

While the present invention has been illustrated by a description of various illustrative embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or any combinations depending on the needs and preferences of the user. However, the present invention itself should only be defined by the appended claims.

What is claimed is:

1. A surgical cannula system comprising:
a cannula having a proximal end, a distal end, and a lumen extending therebetween;
a tissue attachment ring having a lumen extending therethrough, the tissue attachment ring being configured to operably couple to a biological tissue;
a locking mechanism operably coupled to at least one of the cannula or the tissue attachment ring, the locking mechanism having a first locking state and a second locking state; and
a tip coupled to the distal end of the cannula, wherein the tip includes an outer surface for promoting tissue ingrowth;
wherein the cannula is configured to move with respect to the tissue attachment ring when the locking mechanism is in the first locking state and the locking mechanism in the second locking state resists movement of the cannula with respect to the tissue attachment ring.

2. The surgical cannula system of claim 1, wherein the tissue attachment ring further comprises an inner wall defining the lumen, the locking mechanism being operably coupled to the inner wall of the tissue attachment ring.

3. The surgical cannula system of claim 1, wherein the locking mechanism further comprises:
a first locking element operably coupled to the tissue attachment ring; and
a second locking element operably coupled to the cannula, wherein the first and second locking elements cooperate to allow the locking mechanism to move between the first and second locking states.

4. The surgical cannula system of claim 3, wherein the second locking element is operably coupled to the tip of the cannula.

5. The surgical cannula system of claim 3, wherein the locking mechanism further includes a third locking element configured to facilitate the cooperation between the first and second locking elements.

6. The surgical cannula system of claim 5, wherein the second locking element is operably coupled to the tip of the cannula; and
wherein at least a portion of the tip is configured to operably couple to a biological tissue.

7. The surgical cannula system of claim 1, wherein the outer surface comprises a fabric.

8. The surgical cannula system of claim 1, wherein the outer surface comprises a sintered material.

9. The surgical cannula system of claim 1, wherein the locking mechanism is configured to be transitioned from the first locking state to the second locking state when the cannula is directed through the lumen of the tissue attachment ring.

10. The surgical cannula system of claim 9, wherein the tissue attachment ring further comprises an inner wall defining the lumen and the locking mechanism includes a biasing element operably coupled to the inner wall of the tissue attachment ring.

11. The surgical cannula system of claim 1, wherein the locking mechanism is configured to be transitioned from the first locking state to the second locking state after the cannula is positioned within the lumen of the tissue attachment ring.

12. A surgical cannula system comprising:
a cannula having a proximal end, a distal end, and a lumen extending therebetween;
a tissue attachment ring having a lumen extending therethrough, the tissue attachment ring configured to operably couple to a biological tissue; and
a locking mechanism operably coupled to the tissue attachment ring,
wherein the locking mechanism is configured to secure a first position of the cannula extending through and relative to the lumen of the tissue attachment ring;
wherein the tissue attachment ring further comprises an inner wall defining the lumen of the tissue attachment ring and the locking mechanism includes a first locking element operably coupled to the inner wall; and
wherein the first locking element includes an inner groove provided on the inner surface of the lumen of the tissue attachment ring and the second locking element includes a pawl configured to engage the inner groove.

13. The surgical cannula system of claim 12, wherein the locking mechanism is further configured to secure a second position of the cannula relative to the tissue attachment ring, the second position being spaced away from the first position.

14. The surgical cannula system of claim 13, wherein the locking mechanism is further configured to secure the cannula at a position located between the first and second positions.

15. The surgical cannula system of claim 12, wherein the first locking element is configured to form a friction fit with the cannula.

16. The surgical cannula system of claim 12, wherein the locking mechanism further comprises:
a second locking element operably coupled to an outer surface of the cannula, the second locking element configured to cooperate with the first locking element to secure the cannula.

17. The surgical cannula system of claim 16, wherein the locking mechanism further includes a third locking element configured to facilitate the cooperation between the first and second locking elements.

18. The surgical cannula system of claim 12, wherein the tissue attachment ring further comprises:
a tissue in-growth band configured to be positioned between the tissue attachment ring and the biological tissue.

19. The surgical cannula system of claim 12, wherein the tissue attachment ring is a sewing ring configured to be coupled to the biological tissue with one or more sutures.

20. A cannula delivery system comprising:
a cannula having a proximal end, a distal end, and an inner surface defining a lumen therethrough;
a shaft having a proximal end and a distal end, the shaft being configured to extend through the lumen of the cannula;
an obturator tip on the distal end of the shaft, the obturator tip being configured to dilate a puncture in a biological tissue; and
an expandable portion located on the shaft and configured to be expanded so as to engage the inner surface of the cannula,
wherein when the expandable portion is expanded to engage the inner surface of the proximal end of the cannula, the obturator tip extends away from the distal end of the cannula for dilating the puncture.

21. A method of securing a cannula to a surgical site of a biological tissue, the method comprising:
attaching a tissue in-growth band to the surgical site;
attaching a tissue attachment ring to the surgical site such that the tissue in-growth band is positioned between the tissue attachment ring and the surgical site, the tissue attachment ring having a lumen configured to receive the cannula;
directing the cannula through the lumen of the tissue attachment ring and the biological tissue at the surgical site; and
transitioning a locking mechanism from a first locking state to a second locking state, wherein the locking mechanism in the second locking state secures a position of the cannula relative to the tissue attachment ring.

22. A surgical cannula system comprising:
a cannula having a proximal end, a distal end, and a lumen extending therebetween;
a tissue attachment ring having a lumen extending therethrough, the tissue attachment ring configured to operably couple to a biological tissue; and
a locking mechanism operably coupled to at least one of the cannula or the tissue attachment ring, the locking mechanism having a first locking state and a second locking state,
wherein the locking mechanism is configured to secure a first position of the cannula extending through and relative to the lumen of the tissue attachment ring;
wherein the tissue attachment ring further includes a tissue in-growth band configured to be positioned between the tissue attachment ring and the biological tissue; and
wherein the cannula is configured to move with respect to the tissue attachment ring when the locking mechanism is in the first locking state and the locking mechanism in the second locking state resists movement of the cannula with respect to the tissue attachment ring.

* * * * *